US006284253B1

(12) United States Patent
Barr et al.

(10) Patent No.: US 6,284,253 B1
(45) Date of Patent: Sep. 4, 2001

(54) FELINE IMMUNODEFICIENCY VIRUS (FIV) NUCLEOTIDE SEQUENCE

(75) Inventors: Margaret C. Barr, San Diego, CA (US); Roger J. Avery; Claudia A. Sutton, both of Ithaca, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 0 days.

(21) Appl. No.: 09/238,303

(22) Filed: Jan. 28, 1999

Related U.S. Application Data

(60) Provisional application No. 60/072,927, filed on Jan. 29, 1998.

(51) Int. Cl.[7] .......................... A61K 39/21; C07K 16/00; C07H 21/04
(52) U.S. Cl. ................... 424/208.1; 530/388.35; 536/23.72
(58) Field of Search .................. 536/23–72; 530/388.35; 424/208.1

(56) References Cited

U.S. PATENT DOCUMENTS 5,510,106  4/1996  Yamamoto et al. .............. 424/207.1

OTHER PUBLICATIONS

Barr et al., "Isolation of a Highly Cytopathic Lentivirus from a Nondomestic Cat," Journal of Virology, Nov. 1995, pp. 7371–7374.

*Primary Examiner*—Henkyel T. Park
(74) *Attorney, Agent, or Firm*—Hodgson Russ LLP

(57) ABSTRACT

This invention relates to a highly cytopathic and infectious clone constructed from the genomic DNA of a cat FIV. The nucleotide sequences of the infectious clone is disclosed. The nucleotide sequence, and peptides derived therefrom can be used in the detection of, and protection against FIV in both domestic and nondomestic cats. Further, chimeric viruses having the desired immunologic and pathogenic properties can be constructed.

11 Claims, 12 Drawing Sheets

Alignment of GAG proteins from different FIVs

```
             10        20        30        40        50        60        70
              +         +         +         +         +         +         +
Oma3   mgneqgkevkaavkrckevavpgskskkygegnirwairmanvttgrdpgklpeniagvrnlvcdlmei
FIV14  mgngqgrdwkmaikrcsnvavgvggkskkfgegnfrwairmanvstgrepgdipetldqlrlvicdlger
Wo     mgngqgrdwkmaikrcsngavgvggkskkfgegnfrwairmanvstgrepgdipetldqlrlvicdlger
Fiv11  mgngqgrdwkmaikrcsnvavgvggkskkfgegnfrwairmanvstgrepgdipetldqlrlvicdlger
PLV14  mgnnqgkelkaalrracnvtvgegkrskrytegnlmwaikfgnactgrdpadvpetlveirnfihelqdk 80        90       100       110       120       130       140
              +         +         +         +         +         +         +
1      rdkygsnkeieaaiktlkvlgvvgilfmkasntdsavnlweimglnsrPSEKGPGGEEEAMPSAFQAKEQ
2      rekfgsskeidmaivtlkvfavagllnmtvstaaaaenmysqmgldtrPSMKEAGGKEEGPPQ------
3      rekfgsskeidmaiaalkvfavvgllnmtvstaaaaenmytqmgldtrPSTKEAGGKEEGPPQ------
4      rekfgsskeidmaittlkvfavvgllnmtvstaaaaenmytqmgldtrPSTKEAGGKEEGPPQ------
5      lqkfggskelenciktlkvltvagvlklpcqntesaiklyetmgllgpATDKKIEENLEEKPAE-----

150       160       170       180       190       200       210
              +         +         +         +         +         +         +
1      KGVGLRDPQDIAKeypPigvvnggagyvplnprmvaifmekardglgteevllwftafsadltptdmatil
2      ----------aypiqtvngvppqyvaldpkmvsifmekareglggeevqlwftafsanltptdmatli
3      ----------aypiqtvngttqyvaldpkmvsifmekareglggeevqlwftafsanltptdmatli
4      ----------aypiqtvngapqyvaldpkmvsifmekareglggeevqlwftafsanltltdmatli
5      ----------aypvqvangvhqhvsfnprtaaivmekarggslgseeavlwftafsadltatdmasli
```

Figure 6A

```
         150       160       170       180       190       200       210
           +         +         +         +         +         +         +
1  KGVGLRDPQDIAKeypiqvvngqaqyvplnprmvaifmekardglgteevllwftafsadltptdmatli
2  --------------aypiqtvngvpqyvaldpkmvsifmekareglggeevqlwftafsanltptdmatli
3  --------------aypiqtvngttqyvaldpkmvsifmekareglggeevqlwftafsanltptdmatli
4  --------------aypiqtvngapqyvaldpkmvsifmekareglggeevqlwftafsanltltdmatli
5  --------------aypvqvangvhqhvsfnprtaaiwmekargglgseeavlwftafsadltatdmasli 220       230       240       250       260       270       280
           +         +         +         +         +         +         +
1  msapgcaadkeiidtklkeltteeyerthpsdaprplpyftareimgldltqdgqapqfhagrvqgarawy
2  maapgcaadkeildeslkqltaeydrthppdaprplpyftaaeimglgltqeqqaearfaparmqcrawy
3  marpgcaadkeildeslkqltaeydrthppdgprplpyftaaeimglgltqeqqaearfaparmqcrawy
4  maapgcaadkeildeslkqltaeydrthppdgprplpyftaaeimglgltqeqqaeprfaparmqcrawy
5  taapgcaadkkiiddklkeltakyaqdh-pdgprplpyftaeeimglgipqnvqspqygparagarlwf 290       300       310       320       330       340       350
           +         +         +         +         +         +         +
1  iealqylqkiksrspravqmkggpkedyasfidrlyaqidqeqnspevkiylkqslslananpeckkams
2  lealgklaaikakspravqlrggakedyssfidrlfaqidqeqntaevklylkqslsiananadckkams
3  lealgklaaikakspravqlrggakedyssfidrlfaqidqeqntaevklylkqslsiananadckkams
4  lealgklaaikakspravqlrggakedyssfidrlfaqidqeqntaevklylkqslniananadckkams
5  lealghlqkikagepkavtlrggpkesykdfidrlfgqidqeqasdevrdylkqslsisnangecrkamt
```

(CONTINUED)
Figure 6A

```
     360       370       380       390       400       410       420
       +         +         +         +         +         +         +
1  hlkpestleeklracqevgstsykmnmlaqalgqqsqVCQVQQGRGKPQGNNRRPGQSLKCF------
2  hlkpestleeklracqeigspgykmqllaealtkvqvQSKGSGPVCFNCKKPGHLARQCREVKKCN---
3  hlkpestleeklracqeigfpgykmqllaealtkvqvQSKGPGPVCFNCKRPGHLARQCRDVKKCN---
4  hlkpestleeklracqeigspgykmqllaealtkvqvQSKGSGPVCFNCKKPGHLARQCRDVKKCN---
5  hlrpestleeklracqdigstqykmqmlaeafnqmqvNQVQRGGFRGGRGRGRGRGRGRGLGPLN 430       440       450       460       470       480       490
       +         +         +         +         +         +         +
1  ---ncgkpghlarndraprkCNKCGKAGHIATDCWDMQGKQQGNWQKgraaapikqvQQFQTAVSTTQNQQ
2  ---kcgkpghvaakcwggnrkRNSGNWKA------------------graaapvnqm------------
3  ---kcgkpghlaakcwgggkKNSGNWKA------------------graaapvnqv------------
4  ---kcgkpghlaarcwgggkMNSGNWKA------------------graaapvnqv------------
5  CFncgkpghlasqdrqpikCYKCGGSGHLAIDCLGGNDSKNGQ---nrgtaaprqfQVQQNNTLYPSLK- 500       510       520       530       540       550       560
       +         +         +         +         +         +         +
1  QcgliqpsappmesLMDI-
2  -qgavmpsappmeeKLLDL
3  -qgavmpsappmeeKLLDL
4  -qgavmpsappveeKLLD-
5  --emqteptappmei----
```

(CONTINUED)
Figure 6A

| | |
|---|---|
| FIV-Oma3 | ATGGAAAAAGCTAGAGAGATGGATTAGGAACAGAAGAAGTT |
| PLV-14 | ATGGAAAAAGCTAGAGAGGAGGATTAGGATCAGAAGAAGCA |
| FIV-Wo | ATGGAAAAAGCAAGAGAGAAGGATTAGGAGGTGAGGAAGTT |
| FIV-113 | ATGGAAAAAGCAAGAGAAGAAGGATTAGGAGGTGAGGAAGTT |
| FIV-14 | ATGGAAAAAGGCAAGAGAGAGGGATTAGGAGGTGAGGAAGTT |

Figure 6B

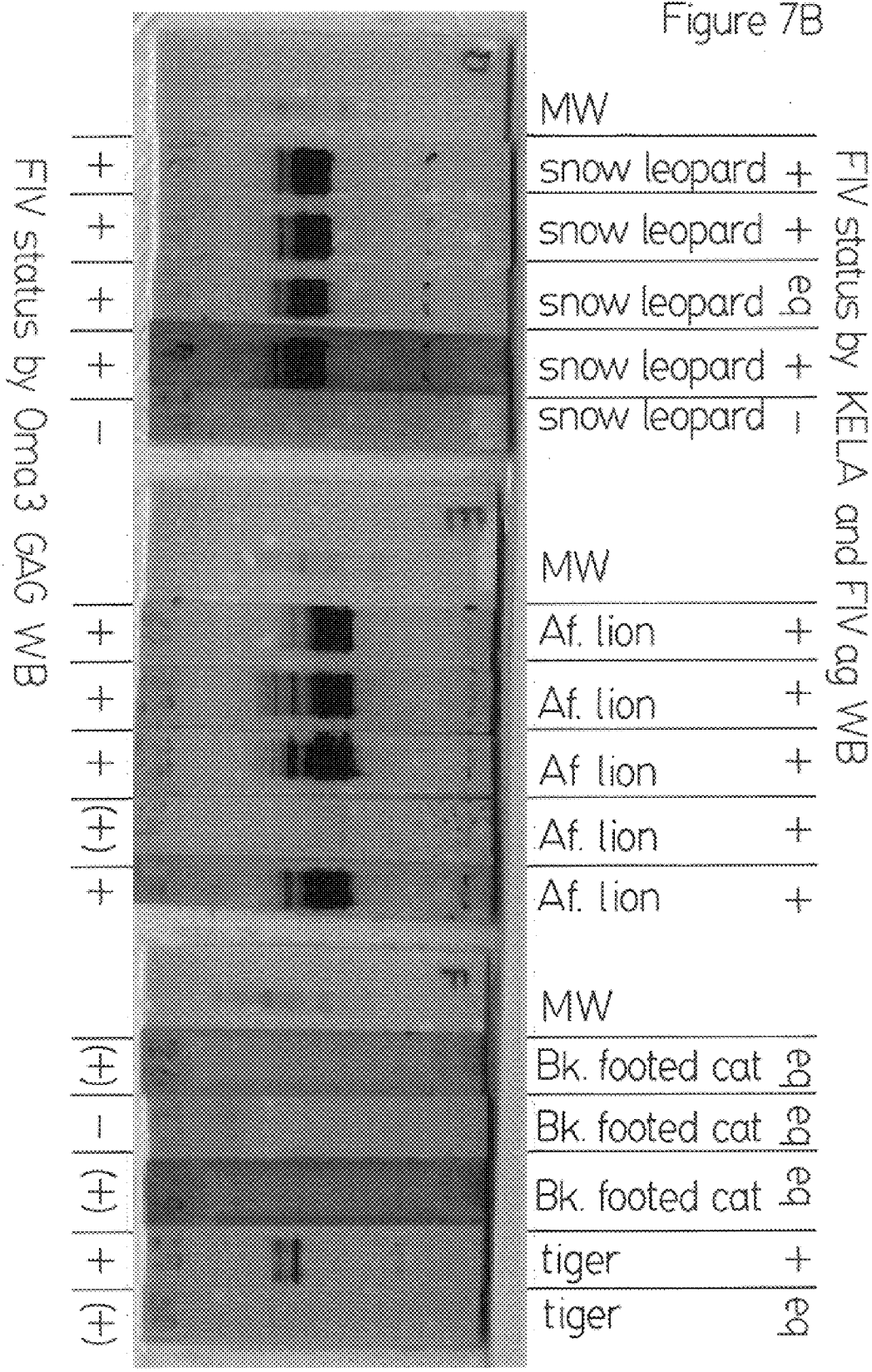

SEQUENCE LISTING

```
<160> NUMBER OF SEQ ID NOS: 17

<210> SEQ ID NO 1
<211> LENGTH: 27
<212> TYPE: DNA
<213> ORGANISM: artificial sequence
<220> FEATURE:
<223> OTHER INFORMATION: completely synthesized; forward primer

<400> SEQUENCE: 1
gcggccgctg ggaggattgg aggtcct                                27
```

<210> SEQ ID NO 2
<211> LENGTH: 20
<212> TYPE: DNA
<213> ORGANISM: artificial sequence
<220> FEATURE:
<223> OTHER INFORMATION: completely synthesized; reverse primer

<400> SEQUENCE: 2
gctcttaagg ctatgtcgca                                          20

<210> SEQ ID NO 3
<211> LENGTH: 21
<212> TYPE: DNA
<213> ORGANISM: artificial sequence
<220> FEATURE:
<223> OTHER INFORMATION: completely synthesized; forward primer

<400> SEQUENCE: 3
tgtccagtgt tagagtcggt a                                        21

<210> SEQ ID NO 4
<211> LENGTH: 27
<212> TYPE: DNA
<213> ORGANISM: artificial sequence
<220> FEATURE:
<223> OTHER INFORMATION: completely synthesized; reverse primer

<400> SEQUENCE: 4
gtcgactgca aggtctccgt ccgaatc                                  27

<210> SEQ ID NO 5
<211> LENGTH: 28
<212> TYPE: DNA
<213> ORGANISM: artificial sequence
<220> FEATURE:
<223> OTHER INFORMATION: completely synthesized; forward primer

<400> SEQUENCE: 5
ggtaccgagt ggtgaagagg attggcag                                 28

<210> SEQ ID NO 6
<211> LENGTH: 21
<212> TYPE: DNA
<213> ORGANISM: artificial sequence
<220> FEATURE:
<223> OTHER INFORMATION: completely synthesized; reverse primer

<400> SEQUENCE: 6
gtcgacttaa ctcttcatcc g                                        21

<210> SEQ ID NO 7
<211> LENGTH: 9751
<212> TYPE: DNA
<213> ORGANISM: Unknown
<220> FEATURE:
<223> OTHER INFORMATION: recombinant viral clone constructed from the
      genomic DNA of a Pallas's cat feline immunodeficiency virus

<400> SEQUENCE: 7
tgggaggatt ggaggtccta aagaccctca gattgtgatg ctcttaaaca          50
gaacattgta acctaggaaa attaaaaaca aaatagcatg ttaagaacag          100
ctgtgtaacc gcaaggctta accacaaacc atatccgtgc taaagtgacg          150
cttgctaggc tagtatgact catttaagtt tccagtagaa tagtatataa          200

-continued

```
gagaaacctt tagtctgttc agggccactt ctttggactt gcaactagct      250 tgctagggc ttgctcctct gaagggtcct caggcacaat aaaattgctcg      300 tgagatttga accctgccgt gtgtctgagt cttttctttc ctgtgaggct      350
ccggattccg ggacggagac cttgcagttg gcgcccgaac agggacttga      400
aggagactct ttcaaagtga agccaaggca atagaaagct gcttagtggg      450
actccctcta ctaccttctg agtgagaccg aaaggttgct cgaaggggag      500
aaaagaggtt gagaggacac agacagtgaa tatccttggt ggagtggcga      550
aagagttaaa ttcaccccct gtaaggcttt gtagtccgga gagaagactg      600
caaagaagac tcttcacgga tcatcaagcc aggtgattcg ccgagggact      650
cgctgacaag gtaagaaaag aagggaccta caggatgggg aatgagcagg      700
gtaaagaagt gaaggctgca gtcaagagat gtaaagaagt agctgtaggt      750
ccggggagta agagcaaaaa atatggagaa ggaaatatca gatgggccat      800
aagaatggca aatgtaacta caggacgaga ccctggtaaa ttgccagaaa      850
acatagcaca ggtaagaaat ttagtatgtg atttaatgga aataagagat      900
aagtatggca gcaataagga atagaggcc gccataaaaa ctttaaaagt      950
tttaggagta gtgggaattc tgtttatgaa ggcttctaat acagactcag     1000
cagtaaattt atgggaaata atgggattaa attcaagacc ctcagaaaaa     1050
ggaccaggag gagaggaaga agcaatgcca tcagcttttc aagccaaaga     1100
gcagaaaggg gtaggattaa gagatccaca agatattgca aaagaatatc     1150
ctatacaagt tgttaatgga caggctcaat atgttccatt gaatccaaga     1200
atggtagcaa tctttatgga aaaagctaga gatggattag gaacagaaga     1250
agttctgtta tggttcacag cattttcagc agacttaaca cctacagata     1300
tggcaacaat attaatgtct gctcctggtt gtgctgcaga taaagaaata     1350
attgatacaa aattaaaaga attaactaca gaatatgaaa gaacacaccc     1400
ctcagatgct ccaagaccat taccttattt tacagcaagg gagataatgg     1450
gattggattt gacacaagat cagcaagcac aacctcaatt tcatgcagga     1500
agagtacaag caagagcttg gtatatagaa gcattgcaat atttacaaaa     1550
aattaaatca agaagtccta gagcagtgca atgaaacaa ggtccaaaag     1600 aggactatgc aagctttata gatagattat atgctcaaat agatcaagaa     1650
caaaatagtc cagaagtaaa aatatatttg aaacaatcat taagtttagc     1700
aaatgctaat cccgagtgca aaaaagccat gtctcattta aaaccagaga     1750
gcactctaga agaaaagttg agagcatgtc aggaggtggg atcaacatcc     1800
tataaaatga atatgttagc acaagcttta caacagcaaa gtcaagtatg     1850
tcaagtacag caaggaagag gaaagccaca aggaaacaat agaagacctg     1900
gccagtcttt gaaatgtttc aattgtggaa aaccaggaca tttagcaagg     1950
aattgtagag cacctagaaa atgtaataaa tgtggcaaag caggccatat     2000
tgcaacagat tgttgggaca tgcagggaaa gcagcaggga aactggcaga     2050
aggggagagc tgctgcccct atcaaacaag tgcagcaatt tcaaacagca     2100
gtatcaacaa ctcagaatca gcaacaatgt caattaatac agccttcggc     2150
```

```
tcctccaatg gagtccctta tggacatcta aagagagata tagaattaat       2200
acatagacca agaattttga tctatgtaaa tgggattcct ataagatttt       2250
taatggatac aggagcagat ataactataa tgaatgcaga agatttaat        2300 atattaaatt caatcccaga tggaatacaa acaatgatag gagtaggagg       2350
aggaaaaaga ggtagaaaat ttagacgagt acatttagaa ataagagatc       2400
ctaatcatag agctcaatgt ttatttggaa atatgtgtat cttagatgac       2450
aatagtttaa cagaacctct gctagggaga gataatatgg ttagatttgg       2500
agcaaagttg gtaatggcaa atatttcaaa taaaattcct atagtaaaag       2550
tgaaaatgaa agatcctagc aaaggaccaa aaattaagca atggcctcta       2600
tcaaaagaaa agatagaagc attaacagaa atagtttata gattggaaaa       2650
agaagggaaa gtaaaaggg cagatccaaa taatccttgg ataccccta        2700 ttttctgtat aaaaaagaaa tcagggaagt ggagaatgtt aatagatttt       2750
agaactctga atgaattaac agaaaaaggt gcagaagttc agttgggact       2800
ccctcatcca gcaggattac aagaaggaa acaagtaaca gtattagata        2850
ttgcagatgc atattttact ataccattag acccagacta tgcaccatat       2900
actgccttta ctctgcccaa aataaataat tcaggtccag gagaaagatt       2950
tgtatggtgt ggtttacctc aaggatgggt attaagtccc ttaatttatc       3000
agagtacatt aaacaatatt ttaaaaccat ttagagaaca gcatccagaa       3050
atagatttat accaatatat ggatgatata tatataggat cagatttagg       3100
aaagaaggag cataaacaaa ttgtagagga attaaggaaa ttattattat       3150
ggtggggatt tgagacgcca gaagacaaat tacaggagca accaccttat       3200
aaatggatgg gatatgaatt atatcctcgg aaatggacta caaacaaa        3250 agaattaata ataccagaag aaccaactct taatgagtta cagaagttag       3300
taggaataat aaattggtca tctcaaataa ttcctggatt aagaattaag       3350
gctttaacta atatgatgaa aggaaatcaa gctttagatt caaaagaag        3400 gtggacagaa gaggctaaga aagaggcaga agaggcaaaa ttggcaatag       3450
aacaacacac acaattagga tattatgatc ctcaacaaca attacatgca       3500
aaattgagta tagtgggtcc acattgtata gggtaccaag tttatcaaaa       3550
agggtctcca gataaaatat tatggtatgg aaaaatgaat agacaaaga        3600 aaaaagcaga aaatacttgc gacatagcct taagagctat atataagatc       3650
agggaagaat caatagtaag gttaggaaaa gaacctattt atgaaatacc       3700
atgttctaga gaagcatggg aatcaaattt gattaatact ccttatttaa       3750
aagcttgccc accacaagta gagtatattc atgcagcaat aatgatacag       3800
aggtctttaa gtatgataaa agaagaacca attgaggtg cagaaacatg        3850 gtatattgat ggaggaagga agaagggaca atcagcaaag gcggcatatt       3900
ggactgataa aggaaaatgg gaagtaatgc aaatagaagg gagtaatcaa       3950
agagcagagg taatggccct attaatggca ttacgatcag ggggagaaga       4000
aatgaatatt gtaacagatt ctcaatatat cctaaatatt ttgagacaaa       4050
aaccagattt gatggaggga ttatggcaag aaatattgga agaaatagaa       4100
aagaaggtag caatttttat agattgggta ccaggtcata aaggcattcc       4150
```

| | |
|---|---|
| tgggaataca gaagtagata acctatgtca aacaatgatg ataatatcag | 4200 |
| gaaatggaat attagataaa ggagaagagg acgcaggata tgatttgctt | 4250 |
| gcagaacaag acatacattt aatgccagga gaagtaagaa tagtccctac | 4300 |
| aggagtaaga ttaatgctgc caaaaggaca ttggggaatg gtagtaggaa | 4350 |
| aatcttcaat tgcaaagcaa ggattggatg ttcttggagg agtaatagat | 4400 |
| gaaggataca gaggggaaat aggtgtaatt atgataaatt tacagaaaag | 4450 |
| atctattact ttaaaagaaa agcaaaaggt agcacaatta ataatcatac | 4500 |
| cttgtaaaca tgaagaattg aaacaagggg aaatagaatt aaattcagaa | 4550 |
| agaggagaaa aagggtatgg atcaacaggt gcatttgcat cttggatgaa | 4600 |
| taacattgaa gaggcagaaa tcaaccatga aaaatttcat tcagatccag | 4650 |
| aatttttaag gactgaattt gggcttccca aacaagttgc agaagaaata | 4700 |
| aaaagaaaat gtcctctatg tatagtgcaa ggggaacaag taatgggaaa | 4750 |
| attaaaagta ggaccaggaa tatggcaaat tgattgtact catttagaag | 4800 |
| gaaagattat actggtcgca gtaaacacag aatcaggata catttgggca | 4850 |
| agaataattc ctcaagagac agcagatatg acagtaaaat atctattaca | 4900 |
| attaatctcg gagcatcatg tgactgaatt acaatcagat aatggaccaa | 4950 |
| attttaataa tgcaaaagta gaaggcatga caggattttt gggaataaaa | 5000 |
| cataaatatg gaattccagg aaaccctcaa tcacaagcct tggtagaaaa | 5050 |
| taccaataga atgttaaaag aatggataaa gaaatttaga ggggaagtaa | 5100 |
| ctactttgga tgcagcattg gcacttgcac tttatgctct taactttaaa | 5150 |
| caaaggggta gaatagggag aatatcccca tatgagttac ttatacagca | 5200 |
| agaatcagac agaataagag attacttttc taaaatacca gcaaataata | 5250 |
| taaaaaattc ttggatttat tataaggata gaagagataa agaatggaag | 5300 |
| ggtccaacac aggtagaata ttggggacaa ggagcagttt taataaaaca | 5350 |
| tccagagcat gggtatatgc tcatccctag gagacacata aggagagttc | 5400 |
| cagaaccctg tactcttcca gaagtggaat gagtggtgaa gaggattggc | 5450 |
| aggtaagtag atctctctat caagtgcttc taggggacc tagaagagct | 5500 |
| atgctctata taggaagtat aatagatgaa aaggaaaagg ctagaaagaa | 5550 |
| aaaagaccta caaaaaagaa tggctagact agaaaataga tttatctatt | 5600 |
| ggttaaggag acaagaaggg atcagatggt cttttcatac aagagattat | 5650 |
| catctaggat ttgtaaaaga gttagttgca ggaagctcta gtcctggatg | 5700 |
| tttaagatta tattgttaca ttagtaatcc attgtggcat aaaaggtata | 5750 |
| ggcctacttt gcagatgaat caagaatttc catatgtaaa ttgttggatt | 5800 |
| acggataaat ttatgtggga tgatatagag aaccagcaaa taatgaagag | 5850 |
| tcctttacct ggyccaggat gggatatagg aatggtggga ttagtaataa | 5900 |
| aagcatattc ctgcccagaa aagaagtatg atgtgacaat accacaggta | 5950 |
| atacggggag aaaaagatcc tcaagaattt tgtgctgatt gttggaatct | 6000 |
| aatatgtgta aggaattcac caccatgtag tctgcaaaga ttggctttaa | 6050 |
| aggcctgtgg caaaccaaca gaaagttggg taggatgttg caaccacaga | 6100 |

```
tttttatctc cttacagatc acctactgac ttattgatag tcagagaagc        6150
tgtaccctat gaagtgttat atcggatgaa gagttaaaag aagaagaatc        6200
tggcgagagc agtagaattt agggaaattt ggatagaagt atttcaggga        6250
gtgacagcta aattagagca gaggcaagca atacaattat atatattagc        6300
tcatagatta gaggtagata acttttttaag aaaacttttta ttttttacaat     6350 ggagattaag atataaccag cctaagggag gttgtaaatg ctggatttgt        6400
ttaggatatt catattggct cttgcagcag cagcagtcta ttttatagat        6450
ttatttgtta ttataggaat tgttttacgc ttttatatag gacaaataat        6500
agaataagag catggcagaa ggaggaagag tagatgtagt agaaagagca        6550
gatgaagaac tagggagaca aggagtagaa gggcatgaat atgcatttgg        6600
gatgaatcca gattggatcg gtccttatga gggagagatg ttattggatt        6650
ttgatatcct tcagtatgta acagaagaag gaccattcag gccaggacac        6700
aaccctttta gagctcccgg aataacggag caagaaagac aagagttatg        6750
tgttatgtta caagacaagc taaaagagat aaaagggacc ataacagaag        6800
gacctcacaa atacctccaa ggtaagtata ggagattaag atatttgcag        6850
tattcagaca tgcaggtaac gcagagtctg gctttattag tctttgatat        6900
tagtcactat cttaggaata agttaggaaa agaagtatat gatatagaag        6950
gagatagaca ggcagaatat aaatttgaaa aaagggttaa aggacgaact        7000
tacaataact gtagatgtag attacttctt ataggtgcag gattcttcta        7050
tacttgtctt ataatagggt tgggatgtct cattagagaa acatcaggag        7100
tgatattggc attggatcct ccttgggtga ttccggtaac aaagatggat        7150
gaaataaatt ttcaatgtca tggaaattat gaggagtgtc cagtgttaga        7200
gtcggtagca acctggaaga cagatttttca atggaattat agtagacctt       7250
ttaatgaaac cataggatta gagcaatatg tagatcagat acaagcaaaa        7300
gcgcttcaag atttacttgg atcctgtcaa aagctatcaa aaaataaatt        7350
aggggttctt caatggagat gcttctacga tagaggtatg aagcaactat        7400
taggattaca aaaataagg atttgtccaa taggaggata tatgttagtt         7450
aggaaaatag atggaaataa ctatacttta agcatgtgca cagaggaaat        7500
agatattaaa atattaaata tgactctaag tcaggaaaaa tatgagcatt        7550
atccatttaa tgatattgtt tggatgggaa acaggtattt taatatgaca        7600
acagcaaata taactcaaca acaagtaaat ataagtataa aatgtgatat        7650
tatagtgcct acagtagtta aagtaaagaa agaatttgca ggatacaata        7700
atgatttctt gggaccatgg ggaggattaa agtataggtc tattcttatt        7750
aggtataaag atttgggcaaa tgttacagat cccccgttag atttaaattg       7800
tactggacta cctggaatag catttaatgg aacagaagca aattatactt        7850
gtgctcaaaa tgctacaatt acctacgaag atatttgtac acaaccagaa        7900
ttgtatgtac catgttatag tccaaattat tcaatgcctg tgatggttca        7950
atgtaaattg catcaagaat atcatcctaa tgatacctat agaaatagta        8000
gcaatgatat gcaagtaatg aggtgtagaa taatgaaaga ggtagaatta        8050
agatttgggg atgaatttat ctcattaaac tttacattgt taagagaycc        8100
```

```
tttttttggct catttgaggg gggctataaa ttttacttgt aatttgacag        8150
gacaattttg ggcttataaa tttaataatg ctacttgggg atatgaaggt        8200
aatggatcag catggaatga atctcttaat tggttagtgc cttataggaa        8250
ctatacaaaa gaaatgtatg tatgggggc atactctgct ataaattata         8300
atcatatttt gttaaaagat tataaacttg ttaaaaaacc gttatatact        8350
ccattaaaat acttaccacc aagaaagaaa agaggattag gattaactct        8400
agctcttgtt actgctacaa ctgcagggtt aataggaaca caacgggga         8450
catctgcact ggcagtgtca ttaaaattaa aagaagtgat gttacaacaa        8500
tcacaaataa atgaagcaac attgggaatg ttaaaaatct acaaagaag         8550
actaaaacag gcagaaagag tgattttaac gttacatcag agagtatcta        8600
ggatagaaaa atatttagaa attcaatatc agttaagagg aatgtgccca        8650
tttaaagaca tctgtgagat accggggaat ggtaattta caaattataa          8700
tgattcttgg gcaataggta gatgggcaga acaagcagaa gaagactggc         8750
agcaatttga acaattgtta aacaatgcaa ccagaacaaa tgaaaatttg         8800
aaaaatgatt tagagaagtt gagtatagat tcctggttat catggaatcc        8850
attagggaat gtgttccaaa tgttaatcac actgataatt ataattggaa        8900
tgggggtaat attgaaagga tgtatattaa actgttgtaa aatcttaatg        8950
gctagtatgg gatataaaag agtagcagaa gaaatggtga tattaccaga        9000
tagtgaatta gatagtgaat cagaaataga attaaatgtg actgagaaag        9050
aaaagaagcc catggtaaat tctggaaagg aggagtctga tgaggaattc        9100
tgaaagaacc caaaagggg atgaggagtt cgcgtgagat acctcctgag         9150
aacagaatga agtaatgggc agtattttct taatcagaaa ctttgtgata        9200
tatgtagata aaacagcaaa gaaaagaaga agaagaagaa aaagggggctt       9250
cagacggatg atgagaaatc tagaaagaag attcgatgca ttgttccatg        9300
actcaccgcc atatgatcca ctgaataatc cggatgtaaa aacactgatg        9350
gactcaaaat aaaagaagg ggtggactgg gaggattgga ggtcctaaag         9400
accctcagat tgtgatgctc ttaaacagaa cattgtaacc taggaaaatt        9450
aaaaacaaaa tagcatgtta agaacagctg tgtaaccgca aggcttaacc        9500
acaaaccata tccgtgctaa agtgacgctt gctaggctag tatgactcat        9550
ttaagttttcc agtagaatag tatataagag aaacctttag tctgttcagg       9600
gccacttctt tggacttgca actagcttgc tagggcttg ctcctctgaa         9650
gggtcctcag gcacaataaa ttgctcgtga gatttgaacc ctgccgtgtg        9700
tctgagtctt ttctttcctg tgaggctccg gattcttacg agaccttgc         9750
a                                                            9751
```

<210> SEQ ID NO 8
<211> LENGTH: 498
<212> TYPE: PRT
<213> ORGANISM: Unknown
<220> FEATURE:
<223> OTHER INFORMATION: protein encoded by the gag gene of a
     recombinant viral clone constructed from the genomic DNA of a
     Pallas's cat feline immunodeficiency virus -continued

```
<400> SEQUENCE: 8

Met Gly Asn Glu Gln Gly Lys Glu Val Lys Ala Ala Val Lys Arg
                  5                  10                  15

Cys Lys Glu Val Ala Val Gly Pro Gly ser Lys Ser Lys Lys Tyr
                 20                  25                  30

Gly Glu Gly Asn Ile Arg Trp Ala Ile Arg Met Ala Asn Val Thr
                 35                  40                  45

Thr Gly Arg Asp Pro Gly Lys Leu Pro Glu Asn Ile Ala Gln Val
                 50                  55                  60

Arg Asn Leu Val Cys Asp Leu Met Glu Ile Arg Asp Lys Tyr Gly
                 65                  70                  75

Ser Asn Lys Glu Ile Glu Ala Ala Ile Lys Thr Leu Lys Val Leu
                 80                  85                  90

Gly Val Val Gly Ile Leu Phe Met Lys Ala Ser Asn Thr Asp Ser
                 95                 100                 105

Ala Val Asn Leu Trp Glu Ile Met Gly Leu Asn Ser Arg Pro Ser
                110                 115                 120

Glu Lys Gly Pro Gly Gly Glu Glu Ala Met Pro Ser Ala Phe
                125                 130                 135

Gln Ala Lys Glu Gln Lys Gly Val Gly Leu Arg Asp Pro Gln Asp
                140                 145                 150

Ile Ala Lys Glu Tyr Pro Ile Gln Val Val Asn Gly Gln Ala Gln
                155                 160                 165

Tyr Val Pro Leu Asn Pro Arg Met Val Ala Ile Phe Met Glu Lys
                170                 175                 180

Ala Arg Asp Gly Leu Gly Thr Glu Glu Val Leu Leu Trp Phe Thr
                185                 190                 195

Ala Phe Ser Ala Asp Leu Thr Pro Thr Asp Met Ala Thr Ile Leu
                200                 205                 210

Met Ser Ala Pro Gly Cys Ala Ala Asp Lys Glu Ile Ile Asp Thr
                215                 220                 225

Lys Leu LyS Glu Leu Thr Thr Glu Tyr Glu Arg Thr His Pro Ser
                230                 235                 240

Asp Ala Pro Arg Pro Leu Pro Tyr Phe Thr Ala Arg Glu Ile Met
                245                 250                 255

Gly Leu Asp Leu Thr Gln Asp Gln Gln Ala Gln Pro Gln Phe His
                260                 265                 270

Ala Gly Arg Val Gln Ala Arg Ala Trp Tyr Ile Glu Ala Leu Gln
                275                 280                 285

Tyr Leu Gln Lys Ile Lys Ser Arg Ser Pro Arg Ala Val Gln Met
                290                 295                 300

Lys Gln Gly Pro Lys Glu Asp Tyr Ala ser Phe Ile Asp Arg Leu
                305                 310                 315

Tyr Ala Gln Ile Asp Gln Glu Gln Asn Ser Pro Glu Val Lys Ile
                320                 325                 330

Tyr Leu Lys Gln Ser Leu Ser Leu Ala Asn Ala Asn Pro Glu Cys
                335                 340                 345

Lys Lys Ala Met Ser His Leu Lys Pro Glu Ser Thr Leu Glu Glu
                350                 355                 360

Lys Leu Arg Ala Cys Gln Glu Val Gly Ser Thr Ser Tyr Lys Met
                365                 370                 375

Asn Met Leu Ala Gln Ala Leu Gln Gln Gln Ser Gln Val Cys Gln
                380                 385                 390
```

```
Val Gln Gln Gly Arg Gly Lys Pro Gln Gly Asn Asn Arg Arg Pro
            395                 400                 405

Gly Gln Ser Leu Lys Cys Phe Asn Cys Gly Lys Pro Gly His Leu
            410                 415                 420

Ala Arg Asn Cys Arg Ala Pro Arg Lys Cys Asn Lys Cys Gly Lys
            425                 430                 435

Ala Gly His Ile Ala Thr Asp Cys Trp Asp Met Gln Gly Lys Gln
            440                 445                 450

Gln Gly Asn Trp Gln Lys Gly Arg Ala Ala Pro Ile Lys Gln
            455                 460                 465

Val Gln Gln Phe Gln Thr Ala Val Ser Thr Thr Gln Asn Gln Gln
            470                 475                 480

Gln Cys Gln Leu Ile Gln Pro Ser Ala Pro Pro Met Glu Ser Leu
            485                 490                 495

Met Asp Ile

<210> SEQ ID NO 9
<211> LENGTH: 1150
<212> TYPE: PRT
<213> ORGANISM: Unknown
<220> FEATURE:
<223> OTHER INFORMATION: protein encoded by the pol gene of a
      recombinant viral clone constructed from the genomic DNA of a
      Pallas's cat feline immunodeficiency virus

<400> SEQUENCE: 9

Met Trp Gln Ser Arg Pro Tyr Cys Asn Arg Leu Leu Gly His Ala
              5                  10                  15

Gly Lys Ala Ala Gly Lys Leu Ala Glu Gly Glu Ser Cys Cys Pro
             20                  25                  30

Tyr Gln Thr Ser Ala Ala Ile Ser Asn Ser Ser Ile Asn Asn Ser
             35                  40                  45

Glu Ser Ala Thr Met Ser Ile Asn Thr Ala Phe Gly Ser Ser Asn
             50                  55                  60

Gly Val Pro Tyr Gly His Leu Lys Arg Asp Ile Glu Leu Ile His
             65                  70                  75

Arg Pro Arg Ile Leu Ile Tyr Val Asn Gly Ile Pro Ile Arg Phe
             80                  85                  90

Leu Met Asp Thr Gly Ala Asp Ile Thr Ile Met Asn Ala Glu Asp
             95                 100                 105

Phe Asn Ile Leu Asn Ser Ile Pro Asp Gly Ile Gln Thr Met Ile
            110                 115                 120

Gly Val Gly Gly Gly Lys Arg Gly Arg Lys Phe Arg Arg Val His
            125                 130                 135

Leu Glu Ile Arg Asp Pro Asn His Arg Ala Gln Cys Leu Phe Gly
            140                 145                 150

Asn Met Cys Ile Leu Asp Asp Asn Ser Leu Thr Glu Pro Leu Leu
            155                 160                 165

Gly Arg Asp Asn Met Val Arg Phe Gly Ala Lys Leu Val Met Ala
            170                 175                 180

Asn Ile Ser Asn Lys Ile Pro Ile Val Lys Val Lys Met Lys Asp
            185                 190                 195

Pro Ser Lys Gly Pro Lys Ile Lys Gln Trp Pro Leu Ser Lys Glu
            200                 205                 210

Lys Ile Glu Ala Leu Thr Glu Ile Val Tyr Arg Leu Glu Lys Glu
```

-continued

```
                    215                 220                 225
Gly Lys Val Lys Arg Ala Asp Pro Asn Asn Pro Trp Asn Thr Pro
                230                 235                 240
Ile Phe Cys Ile Lys Lys Ser Gly Lys Trp Arg Met Leu Ile
                245                 250                 255
Asp Phe Arg Thr Leu Asn Glu Leu Thr Glu LyS Gly Ala Glu Val
                260                 265                 270
Gln Leu Gly Leu Pro His Pro Ala Gly Leu Gln Glu Arg Lys Gln
                275                 280                 285
Val Thr Val Leu Asp Ile Ala Asp Ala Tyr Phe Thr Ile Pro Leu
                290                 295                 300
Asp Pro Asp Tyr Ala Pro Tyr Thr Ala Phe Thr Leu Pro Lys Ile
                305                 310                 315
Asn Asn Ser Gly Pro Gly Glu Arg Phe Val Trp Cys Gly Leu Pro
                320                 325                 330
Gln Gly Trp Val Leu Ser Pro Leu Ile Tyr Gln Ser Thr Leu Asn
                335                 340                 345
Asn Ile Leu Lys Pro Phe Arg Glu Gln His Pro Glu Ile Asp Leu
                350                 355                 360
Tyr Gln Tyr Met Asp Asp Ile Tyr Ile Gly Ser Asp Leu Gly Lys
                365                 370                 375
Lys Glu His Lys Gln Ile Val Glu Glu Leu Arg Lys Leu Leu Leu
                380                 385                 390
Trp Trp Gly Phe Glu Thr Pro Glu Asp Lys Leu Gln Glu Gln Pro
                395                 400                 405
Pro Tyr Lys Trp Met Gly Tyr Glu Leu Tyr Pro Arg Lys Trp Thr
                410                 415                 420
Ile Gln Thr Lys Glu Leu Ile Ile Pro Glu Glu Pro Thr Leu Asn
                425                 430                 435
Glu Leu Gln Lys Leu Val Gly Ile Ile Asn Trp Ser Ser Gln Ile
                440                 445                 450
Ile Pro Gly Leu Arg Ile Lys Ala Leu Thr Asn Met Met Lys Gly
                455                 460                 465
Asn Gln Ala Leu Asp Ser Lys Arg Arg Trp Thr Glu Glu Ala Lys
                470                 475                 480
Lys Glu Ala Glu Glu Ala Lys Leu Ala Ile Glu Gln His Thr Gln
                485                 490                 495
Leu Gly Tyr Tyr Asp Pro Gln Gln Gln Leu His Ala Lys Leu Ser
                500                 505                 510
Ile Val Gly Pro His Cys Ile Gly Tyr Gln Val Tyr Gln Lys Gly
                515                 520                 525
Ser Pro Asp Lys Ile Leu Trp Tyr Gly Lys Met Asn Arg Gln Lys
                530                 535                 540
Lys Lys Ala Glu Asn Thr Cys Asp Ile Ala Leu Arg Ala Ile Tyr
                545                 550                 555
Lys Ile Arg Glu Glu Ser Ile Val Arg Leu Gly Lys Glu Pro Ile
                560                 565                 570
Tyr Glu Ile Pro Cys Ser Arg Glu Ala Trp Glu Ser Asn Leu Ile
                575                 580                 585
Asn Thr Pro Tyr Leu Lys Ala Cys Pro Pro Gln Val Glu Tyr Ile
                590                 595                 600
His Ala Ala Ile Met Ile Gln Arg Ser Leu Ser Met Ile Lys Glu
                605                 610                 615
```

-continued

```
Glu Pro Ile Arg Gly Ala Glu Thr Trp Tyr Ile Asp Gly Gly Arg
                620             625             630
Lys Lys Gly Gln Ser Ala Lys Ala Ala Tyr Trp Thr Asp Lys Gly
                635             640             645
Lys Trp Glu Val Met Gln Ile Glu Gly Ser Asn Gln Arg Ala Glu
                650             655             660
Val Met Ala Leu Leu Met Ala Leu Arg Ser Gly Gly Glu Glu met
                665             670             675
Asn Ile Val Thr Asp Ser Gln Tyr Ile Leu Asn Ile Leu Arg Gln
                680             685             690
Lys Pro Asp Leu Met Glu Gly LeU Trp Gln Glu Ile LeU Glu Glu
                695             700             705
Ile Glu Lys Lys Val Ala Ile Phe Ile Asp Trp val Pro Gly His
                710             715             720
Lys Gly Ile Pro Gly Asn Thr Glu Val Asp Asn Leu Cys Gln Thr
                725             730             735
Met Met Ile Ile Ser Gly Asn Gly Ile Leu Asp Lys Gly Glu Glu
                740             745             750
Asp Ala Gly Tyr Asp Leu Leu Ala Glu Gln Asp Ile His Leu Met
                755             760             765
Pro Gly Glu Val Arg Ile Val Pro Thr Gly Val Arg Leu Met Leu
                770             775             780
Pro Lys Gly His Trp Gly Met Val Val Gly Lys Ser Ser Ile Ala
                785             790             795
Lys Gln Gly Leu Asp Val Leu Gly Gly Val Ile Asp Glu Gly Tyr
                800             805             810
Arg Gly Glu Ile Gly Val Ile Met Ile Asn Leu Gln Lys Arg Ser
                815             820             825
Ile Thr Leu Lys Glu Lys Gln Lys Val Ala Gln Leu Ile Ile Ile
                830             835             840
Pro Cys Lys His Glu Glu Leu Lys Gln Gly Glu Ile Glu Leu Asn
                845             850             855
Ser Glu Arg Gly Glu Lys Gly Tyr Gly Ser Thr Gly Ala Phe Ala
                860             865             870
Ser Trp Met Asn Asn Ile Glu Glu Ala Glu Ile Asn His Glu Lys
                875             880             885
Phe His Ser Asp Pro Glu Phe Leu Arg Thr Glu Phe Gly Leu Pro
                890             895             900
Lys Gln Val Ala Glu Glu Ile Lys Arg Lys Cys Pro Leu Cys Ile
                905             910             915
Val Gln Gly Glu Gln Val Met Gly Lys Leu Lys Val Gly Pro Gly
                920             925             930
Ile Trp Gln Ile Asp Cys Thr His Leu Glu Gly Lys Ile Ile Leu
                935             940             945
Val Ala Val Asn Thr Glu Ser Gly Tyr Ile Trp Ala Arg Ile Ile
                950             955             960
Pro Gln Glu Thr Ala Asp Met Thr Val Lys Tyr Leu Leu Gln Leu
                965             970             975
Ile Ser Glu His His Val Thr Glu Leu Gln Ser Asp Asn Gly Pro
                980             985             990
Asn Phe Asn Asn Ala Lys Val Glu Gly Met Thr Gly Phe Leu Gly
                995             1000            1005
```

-continued

```
Ile Lys His Lys Tyr Gly Ile Pro Gly Asn Pro Gln Ser Gln Ala
            1010                1015                1020

Leu Val Glu Asn Thr Asn Arg Met Leu Lys Glu Trp Ile Lys Lys
            1025                1030                1035

Phe Arg Gly Glu Val Thr Thr Leu Asp Ala Ala Leu Ala Leu Ala
            1040                1045                1050

Leu Tyr Ala Leu Asn Phe Lys Gln Arg Gly Arg Ile Gly Arg Ile
            1055                1060                1065

Ser Pro Tyr Glu Leu Leu Ile Gln Gln Glu Ser Asp Arg Ile Arg
            1070                1075                1080

Asp Tyr Phe Ser Lys Ile Pro Ala Asn Asn Ile Lys Asn Ser Trp
            1085                1090                1095

Ile Tyr Tyr Lys Asp Arg Arg Asp Lys Glu Trp Lys Gly Pro Thr
            1100                1105                1110

Gln Val Glu Tyr Trp Gly Gln Gly Ala Val Leu Ile Lys His Pro
            1115                1120                1125

Glu His Gly Tyr Met Leu Ile Pro Arg Arg His Ile Arg Arg Val
            1130                1135                1140

Pro Glu Pro Cys Thr Leu Pro Glu Val Glu
            1145                1150

<210> SEQ ID NO 10
<211> LENGTH: 252
<212> TYPE: PRT
<213> ORGANISM: Unknown
<220> FEATURE:
<223> OTHER INFORMATION: protein encoded by the vif gene of a
      recombinant viral clone constructed from the genomic DNA of a
      Pallas's cat feline immunodeficiency virus

<400> SEQUENCE: 10

Met Ser Gly Glu Glu Asp Trp Gln Val Ser Arg Ser Leu Tyr Gln
              5                  10                  15

Val Leu Leu Gly Gly Pro Arg Arg Ala Met Leu Tyr Ile Gly Ser
             20                  25                  30

Ile Ile Asp Glu Lys Glu Lys Ala Arg Lys Lys Asp Leu Gln
             35                  40                  45

Lys Arg Met Ala Arg Leu Glu Asn Arg Phe Ile Tyr Trp Leu Arg
             50                  55                  60

Arg Gln Glu Gly Ile Arg Trp Ser Phe His Thr Arg Asp Tyr His
             65                  70                  75

Leu Gly Phe Val Lys Glu Leu Val Ala Gly Ser Ser Pro Gly
             80                  85                  90

Cys Leu Arg Leu Tyr Cys Tyr Ile Ser Asn Pro Leu Trp His Lys
             95                 100                 105

Arg Tyr Arg Pro Thr Leu Gln Met Asn Gln Glu Phe Pro Tyr Val
            110                 115                 120

Asn Cys Trp Ile Thr Asp Lys Phe Met Trp Asp Asp Ile Glu Asn
            125                 130                 135

Gln Gln Ile Met Lys Ser Pro Leu Pro Gly Pro Gly Trp Asp Ile
            140                 145                 150

Gly met Val Gly Leu Val Ile Lys Ala Tyr Ser Cys Pro Glu Lys
            155                 160                 165

Lys Tyr Asp Val Thr Ile Pro Gln Val Ile Arg Gly Glu Lys Asp
            170                 175                 180

Pro Gln Glu Phe Cys Ala Asp Cys Trp Asn Leu Ile Cys Val Arg
```

-continued

```
                185                 190                 195
Asn Ser Pro Pro Cys Ser Leu Gln Arg Leu Ala Leu Lys Ala Cys
                200                 205                 210

Gly Lys Pro Thr Glu Ser Trp Val Gly Cys Cys Asn His Arg Phe
                215                 220                 225

Leu Ser Pro Tyr Arg Ser Pro Thr Asp Leu Leu Ile Val Arg Glu
                230                 235                 240

Ala Val Pro Tyr Glu Val Leu Tyr Arg Met Lys Ser
                245                 250

<210> SEQ ID NO 11
<211> LENGTH: 863
<212> TYPE: PRT
<213> ORGANISM: Unknown
<220> FEATURE:
<223> OTHER INFORMATION: protein encoded by the env gene of a
      recombinant viral clone constructed from the genomic DNA of a
      Pallas's cat feline immunodeficiency virus

<400> SEQUENCE: 11

Met Ala Glu Gly Gly Arg Val Asp Val Val Glu Arg Ala Asp Glu
                5                   10                  15

Glu Leu Gly Arg Gln Gly Val Glu Gly His Glu Tyr Ala Phe Gly
                20                  25                  30

Met Asn Pro Asp Trp Ile Gly Pro Tyr Glu Gly Glu Met Leu Leu
                35                  40                  45

Asp Phe Asp Ile Leu Gln Tyr Val Thr Glu Glu Gly Pro Phe Arg
                50                  65                  60

Pro Gly His Asn Pro Phe Arg Ala Pro Gly Ile Thr Glu Gln Glu
                65                  70                  75

Arg Gln Glu Leu Cys Val Met Leu Gln Asp Lys Leu Lys Glu Ile
                80                  85                  90

Lys Gly Thr Ile Thr Glu Gly Pro His Lys Ile Pro Pro Gly Lys
                95                  100                 105

Tyr Arg Arg Leu Arg Tyr Leu Gln Tyr Ser Asp Met Gln Val Thr
                110                 115                 120

Gln Ser Leu Ala Leu Leu Val Phe Asp Ile Ser His Tyr Leu Arg
                125                 130                 135

Asn Lys Leu Gly Lys Glu Val Tyr Asp Ile Glu Gly Asp Arg Gln
                140                 145                 150

Ala Glu Tyr Lys Phe Glu Lys Arg Val Lys Gly Arg Thr Tyr Asn
                155                 160                 165

Asn Cys Arg Cys Arg Leu Leu Leu Ile Gly Ala Gly Phe Phe Tyr
                170                 175                 180

Thr Cys Leu Ile Ile Gly Leu Gly Cys Leu Ile Arg Glu Thr ser
                185                 190                 195

Gly Val Ile Leu Ala Leu Asp Pro Pro Trp Val Ile Pro Val Thr
                200                 205                 210

Lys Met Asp Glu Ile Asn Phe Gln Cys His Gly Asn Tyr Glu Glu
                215                 220                 225

Cys Pro Val Leu Glu Ser Val Ala Thr Trp Lys Thr Asp Phe Gln
                230                 235                 240

Trp Asn Tyr Ser Arg Pro Phe Asn Glu Thr Ile Gly Leu Glu Gln
                245                 250                 255

Tyr Val Asp Gln Ile Gln Ala Lys Ala Leu Gln Asp Leu Leu Gly
                260                 265                 270
```

-continued

```
Ser Cys Gln Lys Leu Ser Lys Asn Lys Leu Gly Val Leu Gln Trp
                275                 280                 285
Arg Cys Phe Tyr Asp Arg Gly Met Lys Gln Leu Leu Gly Leu Gln
                290                 295                 300
Lys Ile Arg Ile Cys Pro Ile Gly Gly Tyr Met Leu Val Arg Lys
                305                 310                 315
Ile Asp Gly Asn Asn Tyr Thr Leu Ser Met Cys Thr Glu Glu Ile
                320                 325                 330
Asp Ile Lys Ile Leu Asn Met Thr Leu Ser Gln Glu Lys Tyr Glu
                335                 340                 345
His Tyr Pro Phe Asn Asp Ile Val Trp Met Gly Asn Arg Tyr Phe
                350                 355                 360
Asn Met Thr Thr Ala Asn Ile Thr Gln Gln Gln Val Asn Ile Ser
                365                 370                 375
Ile Lys Cys Asp Ile Ile Val Pro Thr Val Lys Val Lys Lys
                380                 385                 390
Glu Phe Ala Gly Tyr Asn Asn Asp Phe Leu Gly Pro Trp Gly Gly
                395                 400                 405
Leu Lys Tyr Arg Ser Ile Leu Ile Arg Tyr Lys Asp Trp Ala Asn
                410                 415                 420
Val Thr Asp Pro Pro Leu Asp Leu Asn Cys Thr Gly Leu Pro Gly
                425                 430                 435
Ile Ala Phe Asn Gly Thr Glu Ala Asn Tyr Thr Cys Ala Gln Asn
                440                 445                 450
Ala Thr Ile Thr Tyr Gly Asp Ile Cys Thr Gln Pro Glu Leu Tyr
                455                 460                 465
Val Pro Cys Tyr Ser Pro Asn Tyr Ser Met Pro Val Met Val Gln
                470                 475                 480
Cys Lys Leu His Gln Glu Tyr His Pro Asn Asp Thr Tyr Arg Asn
                485                 490                 495
Ser Ser Asn Asp Met Gln Val Met Arg Cys Arg Ile Met Lys Glu
                500                 505                 510
Val Glu Leu Arg Phe Gly Asp Glu Phe Ile Ser Leu Asn Phe Thr
                515                 520                 525
Leu Leu Arg Asp Pro Phe Leu Ala His Leu Arg Gly Ala Ile Asn
                530                 535                 540
Phe Thr Cys Asn Leu Thr Gly Gln Phe Trp Ala Tyr Lys Phe Asn
                545                 550                 555
Asn Ala Thr Trp Gly Tyr Glu Gly Asn Gly Ser Ala Trp Asn Glu
                560                 565                 570
Ser Leu Asn Trp Leu Val Pro Tyr Arg Asn Tyr Thr Lys Glu Met
                575                 580                 585
Tyr Val Trp Gly Ala Tyr Ser Ala Ile Asn Tyr Asn His Ile Leu
                590                 595                 600
Leu Lys Asp Tyr Lys Leu Val Lys Pro Leu Tyr Thr Pro Leu
                605                 610                 615
Lys Tyr Leu Pro Pro Arg Lys Lys Arg Gly Leu Gly Leu Thr Leu
                620                 625                 630
Ala Leu Val Thr Ala Thr Thr Ala Gly Leu Ile Gly Thr Thr Thr
                635                 640                 645
Gly Thr Ser Ala Leu Ala Val Ser Leu Lys Leu Lys Glu Val Met
                650                 655                 660
```

```
Leu Gln Gln Ser Gln Ile Asn Glu Ala Thr Leu Gly Met Leu Lys
            665                 670                 675

Ile Leu Gln Arg Arg Leu Lys Gln Ala Glu Arg Val Ile Leu Thr
            680                 685                 690

Leu His Gln Arg Val Ser Arg Ile Glu Arg Tyr Leu Glu Ile Gln
            695                 700                 705

Tyr Gln Leu Arg Gly Met Cys Pro Phe Lys Asp Ile Cys Glu Ile
            710                 715                 720

Pro Gly Asn Gly Asn Phe Thr Asn Tyr Asn Asp Ser Trp Ala Ile
            725                 730                 735

Gly Arg Trp Ala Glu Gln Ala Glu Glu Asp Trp Gln Phe Glu
            740                 745                 750

Gln Leu Leu Asn Asn Ala Thr Arg Thr Asn Glu Asn Leu Lys Asn
            755                 760                 765

Asp Leu Glu Lys Leu Ser Ile Asp Ser Trp Leu Ser Trp Asn Pro
            770                 775                 780

Leu Gly Asn Val Phe Gln Met Leu Ile Thr Leu Ile Ile Ile Ile
            785                 790                 795

Gly Met Gly Val Ile Leu Lys Gly Cys Ile Leu Asn Cys Cys Lys
            800                 805                 810

Ile Leu Met Ala Ser Met Gly Tyr Lys Arg Val Ala Glu Glu Met
            815                 820                 825

Val Ile Leu Pro Asp Ser Glu Leu Asp Ser Glu Ser Glu Ile Glu
            830                 835                 840

Leu Asn Val Thr Glu Lys Glu Lys Lys Pro Met Val Asn Ser Gly
            845                 850                 855

Lys Glu Glu Ser Asp Glu Glu Phe
            860

<210> SEQ ID NO 12
<211> LENGTH: 51
<212> TYPE: PRT
<213> ORGANISM: Unknown
<220> FEATURE:
<223> OTHER INFORMATION: protein encoded by the open reading frame A
      (orfA) of a recombinant viral clone constructed from the genomic
      DNA of a Pallas's cat feline immunodeficiency virus

<400> SEQUENCE: 12

Met Gly Asn Asn Gly Ile Lys Phe Lys Thr Leu Arg Lys Arg Thr
             5                  10                  15

Arg Arg Arg Gly Arg Ser Asn Ala Ile Ser Phe Ser Ser Gln Arg
            20                  25                  30

Ala Glu Arg Gly Arg Ile Lys Arg Ser Thr Arg Tyr Cys Lys Arg
            35                  40                  45

Ile Ser Tyr Thr Ser Cys
            50

<210> SEQ ID NO 13
<211> LENGTH: 39
<212> TYPE: PRT
<213> ORGANISM: Unknown
<220> FEATURE:
<223> OTHER INFORMATION: protein encoded by the open reading frame B
      (orfB) of a recombinant viral clone constructed from the genomic
      DNA of a Pallas's cat feline immunodeficiency virus

<400> SEQUENCE: 13

Met Leu Asp Leu Phe Arg Ile Phe Ile Leu Ala Leu Ala Ala Ala
```

-continued 5 10 15

Ala Val Tyr Phe Ile Asp Leu Phe Val Ile Ile Gly Ile Val Leu
20 25 30

Arg Phe Tyr Ile Gly Gln Ile Ile Glu
35

<210> SEQ ID NO 14
<211> LENGTH: 38
<212> TYPE: PRT
<213> ORGANISM: Unknown
<220> FEATURE:
<223> OTHER INFORMATION: protein encoded by the open reading frame C (orfC) of a recombinant viral clone constructed from the genomic DNA of a Pallas's cat feline immunodeficiency virus

<400> SEQUENCE: 14

Met Glu Gln Lys Gln Ile Ile Leu Val Leu Lys Met Leu Gln Leu
5 10 15

Pro Thr Glu Ile Phe Val His Asn Gln Asn Cys Met Tyr His Val
20 25 30

Ile Val Gln Ile Ile Gln Cys Leu
35

<210> SEQ ID NO 15
<211> LENGTH: 65
<212> TYPE: PRT
<213> ORGANISM: Unknown
<220> FEATURE:
<223> OTHER INFORMATION: protein encoded by the open reading frame (orfE) of a recombinant viral clone constructed from the genomic DNA of a Pallas's cat feline immunodeficiency virus

<400> SEQUENCE: 15

Met Gly Ser Ile Phe Leu Ile Arg Asn Phe Val Ile Tyr val Asp
5 10 15

Lys Thr Ala Lys Lys Arg Arg Arg Arg Arg Lys Arg Gly Phe Arg
20 25 30

Arg Met Met Arg Asn Leu Glu Arg Arg Phe Asp Ala Leu Phe His
35 40 45

Asp Ser Pro Pro Tyr Asp Pro Leu Asn Asn Pro Asp Val Lys Thr
50 55 60

Leu Met Asp Ser Lys
65

<210> SEQ ID NO 16
<211> LENGTH: 26
<212> TYPE: DNA
<213> ORGANISM: artificial sequence
<220> FEATURE:
<221> NAME/KEY: a,t,g or c
<222> LOCATION: 14
<223> OTHER INFORMATION: completely synthesized; degenerate primer

<400> SEQUENCE: 16
ccgatccdca yccngsagga ytamaa 26

<210> SEQ ID NO 17
<211> LENGTH: 28
<212> TYPE: DNA
<213> ORGANISM: artificial sequence -continued

```
<220> FEATURE:
<223> OTHER INFORMATION: completely synthesized; degenerate primer

<400> SEQUENCE: 17
ggtctagayr yarttcataa cccakcca                                              28
```

FELINE IMMUNODEFICIENCY VIRUS (FIV) NUCLEOTIDE SEQUENCE

This application claims the priority of provisional application Ser. No. 60/072,927, filed on Jan. 29, 1998, which disclosure is incorporated herein by reference.

This invention was made with Government support under Grant No. RR09889-01-A1 awarded by the National Institutes of Health. The Government has certain rights in the invention.

FIELD OF THE INVENTION

The present invention relates generally to detection of and vaccination against Feline immunodeficiency virus (FIV). More particularly, the invention relates to a highly cytopathic and infectious proviral clone constructed from the genomic DNA of a Pallas's cat FIV. The nucleotide sequences, antigens and chimeric viruses derived from the reconstructed clone can be used for the detection of and protection against FIV.

BACKGROUND OF THE INVENTION

Feline immunodeficiency virus, (FIV) a lentivirus of cats is associated with feline acquired immunodeficiency syndrome (AIDS) (see Pederson et al., 1987, Science 235:790). Under natural conditions, cats experience an asymptomatic carrier state for years following initial FIV infection before developing an AIDS like disease. Cats experimentally infected with FIV exhibit signs of acute infection which resolve over a few months. Disorders associated with FIV infection include abortion, alopecia, anemia, gingivitis/stomatitis, upper respiratory infections, chronic enteritis, diarrhea, neurological abnormalities, and recurrent ocular disease, see R. English et al., 1990, *J. Am. Vet. Med. Assoc.,* 196:116; N. Pederson et al., 1989, *Vet. Immonol. Immunopathol.* 21:111, J. Yamamoto et al., 1989, *J. Am. Vet. Med. Assoc.* 194:213.

FIV and the human immunodeficiency virus, HIV-1, belong to the lentivirus subfamily of retroviruses and have similar morphology, protein composition and Mg++ dependency of their reverse transcriptases (RT). Pederson et al., 1987, supra; Pederson et al., 1989, supra. They both display tropism for T lymphocytes and monocytes and are capable inducing these cells to form syncytia (see Brunner and Pederson, 1989, *J. Virol.* 63:5483). The etiology and pathogenesis of FIV infection closely resembles those of human immunodeficiency virus (HIV) and simian immunodeficiency virus (SIV), which cause acquired immunodeficiency syndrome in humans and primates respectively. Thus, FIV infection in cats provides a valuable animal model for human immunodeficiency virus-1 (HIV-1) induced AIDS. The pathogenesis of HIV-1 infection has been attributed to virus-induced reduction of CD4+ lymphocyte numbers and function, resulting in decreased immune responsiveness and subsequently severe secondary infections (see M. McChesney and M. Oldstone, 1989, *Ad.Immunol.,* 4:335).

The discovery of feline T-lymphotrophic lentivirus (now known as Feline Immunodeficiency virus) was first reported by Pederson et al., 1987, supra at 790–793. Cloning and sequence analysis of FIV have been reported by Olmsted et al., 1989. *Proc Natl. Acad. Sci. USA.* 86:4355–4360; and Talbott et al., 1989, *Proc. Natl. Acad. Sci., USA* 86:5743–5747. Molecular clones of several domestic cat isolates of FIV have been sequenced (Maki et al., 1992, *Arch. Virol.* 123:29–45; Miyazawa et al., 1991 *J. Gen Virol.* 74:1573–1580; Olmsted et al., 1989, *Proc. Natl. Acad. Sci. USA,* 86:2448–2452; Phillips et al., 1990 *J. Virol.* 64:4605–4613; and Talbott et al., 1989, *Proc. Natl. Acad. Sci. USA,* 86:5743–5747). However, the full nucleotide sequence of only two non-domestic cat lentivirus (isolated from a puma and a Pallas' cat) has been reported (Langley et al., 1994, *Virology* 202:853–864; Barr et al., 1995 *J. Virol.* 69:7371–7374; deposited as accession no. U56928). Nucleotide sequence data from short regions of the pol gene have been obtained for lentivirus infecting additional pumas, and lion (Brown et al., 1994, *J. Virol.* 68:5953–5968; Olmsted et al., 1992, *J. Virol.* 66:6008–6018). The FIV provirus includes the structural genes for group-specific antigens (gag gene), envelope proteins (env gene) and reverse transcriptase (pol gene), as well as several short open reading frames similar to those of other lentiviruses. The gag gene of FIV has been reported to encode a polypeptide of about 450 amino acids, which undergoes posttranslational modification. (Talbott et al, 1989, supra; Phillips et al., 1990, supra). The gag gene is thought to be highly conserved among FIV strains (Phillips et al., 1990, supra).

Based on the available cloning and sequencing analysis data, the various species of cats appear to be infected with their own unique lentiviruses. This is similar to the significant strain differences noted among human (Oram et al. 1990—*AIDS Res. Hum. Retroviruses* 6:1073–1078) and simian (Fomsgaard et al 1991, *Virology* 182:397–402) immunodeficiency virus isolates. These differences have an impact on the diagnostic procedures, therapeutics and vaccines, making the task of developing broad-spectrum vaccines or detection systems more difficult. Similarly, because FIV isolates from domestic cats exhibit heterogeneity at both the cellular and molecular level (Miyazawa et al., 1991, supra; Phillips et al., 1991, supra), and because these differences are more pronounced between isolates of FIV from domestic and nondomestic cats, vaccines and detection systems for screening various species of domestic and nondomestic cats are not currently available.

In the past, FIV antigens have been used to elicit antibodies which may protect a cat against virus infection and/or replication. These antigens include the FIV gag protein and the env protein. However, these antigens are typically not cross reactive with antibodies from other species and hence are not expected to protect a broad range of species. It would be desirable to identify antigens that have a broad specificity, and as a result cross react with antibodies from different species of cat. Such antigens would be useful for detection and/or immunization purposes.

It would also be useful to identify FIV related viruses that can be used as antigens for a broad range of species of cats. None of the isolated FIVs express broad specificity polypeptides. Thus, it would be useful to construct chimeric viruses expressing polypeptides of desired specificity. Shibata et al. 1991, *J. Virol.* 65:3514–3522, reported the preparation of a chimeric virus containing HIV-1 tat, rev, and env genes in a SIV provirus. The SIV provirus did not contain functional vpr and nef genes, which are considered to be non essential for viral replication and infection of tissue cultured cells. The chimeric viruses replicated in macaque peripheral blood mononuclear cells. However, when used for infecting macaques, the level of virus replication was low and the infection did not persist beyond two months (see U.S. Pat. No. 5,664,195). Thus, the construction of chimeric viruses having desired biological properties like high immunogenicity and low cytopathicity has as yet not met with much success.

SUMMARY OF THE INVENTION

A Pallas's cat FIV isolate (FIV-Oma) was observed to elicit a unique immune response in domestic cats. After an initial seropositive period, the cats had undetectable levels of antibodies in their serum. A highly cytopathic and infectious clone (FIV-Oma3) has been constructed from the genomic library of this FIV. The recombinant virus of the present invention is highly cytopathic and infectious in culture.

Antigens from the Pallas's cat FIV (FIV-Oma) and from the recombinant virus, FIV-Oma3, have been observed to have a broad specificity for various species of FIVs, in contrast to most of the antigens from other domestic or non-domestic cats. Hence, it is an object of the present invention to provide antigens having a broad specificity for immunization of cats.

Another object of the present invention is to provide a detection system based on the antigens having a broad specificity that will identify FIV infection in both domestic and non-domestic cats.

A further object of the present invention is to provide one or more nucleic acid sequences, encoding for FIV polypeptide(s) which can be used as probes for the detection of FIVs and can be inserted for expression into recombinant viral vectors.

A still further object of the present invention is to provide a system for evaluation of therapeutic agents that inhibit the cytopathic effects of lentiviruses.

The recombinant virus, FIV-Oma3 is highly cytopathic in culture. This clone can be used to identify gene sequences that are involved in conferring immunogenicity and cytopathicity in FIV strains. Further, chimeric viruses can be constructed which are immunogenic and highly cytopathic in culture. Alternatively, chimeric viruses can be constructed that are pathogenic in cats. Thus, one further object of the present invention is to provide chimeric viruses having the desired combination of genes which can be used as vaccines to induce antibodies to protect against virus infection and/or replication.

BRIEF DESCRIPTION OF THE FIGURES

FIG. 6A is a schematic presentation of amino acid sequences of gag protein from FIV strains illustrating regions of similarity.

FIG. 6B is a schematic presentation of the nucleotide sequence corresponding to the first boxed region of FIG. 6A.

FIGS. 7A, 7B and 7c are representations of western blots illustrating the detection of FIV using the gag protein from FIV-Oma3 and illustrating a comparison of FIV status as determined by gag western blot and by conventional methods.

DETAILED DESCRIPTION OF THE INVENTION

Figure 1A:
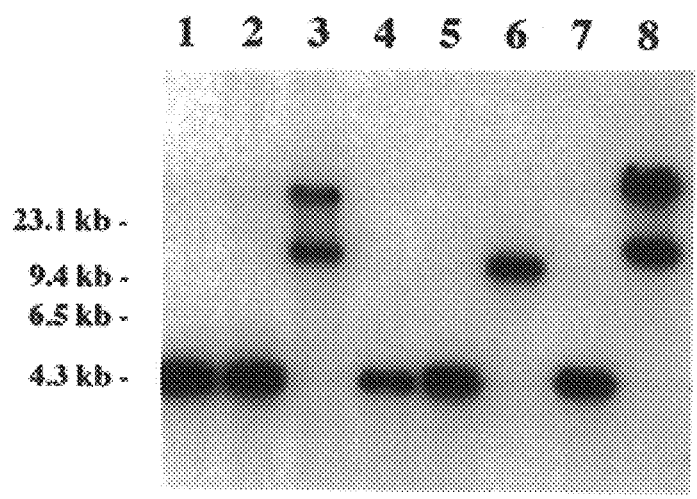
FIG. 1A is a photomicrograph of a Southern blot illustrating endonuclease Sacd digestion of the lambda clones of FIV-Oma.

FIV is a feline immunodeficiency virus classified as a retrovirus and more specifically as a lentivirus, which is tropic for the T-lymphocytes of the host. FIV isolates from domestic and non-domestic cats exhibit heterogeneity at both cellular and molecular levels. The isolation and characterization of a highly cytopathic lentivirus from a young adult male Pallas' cat has been previously reported (Barr et al., 1995). The Pallas' cat (*Otocolobus manul*), was imported into the United States with three other Pallas' cats. During quarantine, the cat tested positive for FIV as detected with an enzyme-linked immunosorbent assay (ELISA) (PetChek FIV Antibody Kit; IDEXX corp.) On immunoblot analysis, the cat's serum reacted with the major core protein, p24 of the prototype domestic cat isolate, FIV-Fca (Petaluma) see Barr et al., 1995, supra at 7371. The other Pallas' cats tested negative in both antibody assays. Hematological values for the seropositive Pallas' cat were within normal ranges, and the cat appeared clinically normal, however, the cat was infected with a Trypanosoma species and *Hepatozoon canis*. In addition, the FIV-positive cat's CD4+/CD8+T-cell ratio was substantially lower than those of the three seronegative cats. Isolated FIV from the FIV-positive cat elicited a unique immune response in domestic cats (Barr et al. 1995). The cats seroconverted, with antibody levels peaking at 7–9 weeks post-infection, then decreased to low levels over the next 12 weeks. Although the initial response of these cats to FIV-Pallas was similar to that seen when cats are infected with domestic cat FIV, the subsequent loss of antibody was unique. Definitions The term "chimeric virus" for the purposes of specification and claims refers to a recombinant virus in the construction of which, portions of gene sequences, or minor modifications thereof that do not result in modified biological activity, from any of the FIV strains, have been used. Chimeric viruses may be formed by recombinations of gene sequences of two or more FIV strains.

The term "immunologically related" for the purposes of specification and claims refers to various strains that display serological cross-reactivity with polypeptides expressed by the reconstructed viruses or variations thereof.

The term "serological cross reactivity" for the purposes of specifications and claims refers to the ability of an antiserum or antibody specific for the antigen(s) from a given strain to react with antigen(s) from other FIV strains. The FIV strains may include those both from domestic and non-domestic cats. Serological cross-reactivity may be determined by any standard immunoassay known in the art including, but not limited to ELISA, western blotting, and immunoblotting.

The term "polypeptide" as used herein for the purposes of specification and claims refers to a chain of amino acids, having a biological function, and does not refer to a specific length of chain. The polypeptide may be modified in vivo or in vitro, for example, by glycosylation, amidation, phosphorylation, carboxylation, or substitution without changing the primary biological function.

Isolation of FIV from Pallas' cat was carried out by the method of Barr et al. 1995, which method is hereby incorporated by reference. A culture of this virus has been deposited with the ATCC and has the accession no. .

The method of the present invention comprises first propagating and cultivating the Pallas's cat FIV (FIV-Oma) in established cell lines by methods well known in the art and as described in more details in the embodiments described herein.

A genomic DNA library can be constructed by standard methods well known in the art. Typically, following partial digestion of genomic DNA and reaction with Klenow polymerase in the presence of adenosine triphosphate (ATP) and guanosine triphosphate (GTP), fragments of 10–20 kb are isolated and ligated to lambda phage arms. The resultant phage is used to infect *Escherichia coli* (*E. coli*) and plated on tryptone broth to form plaques. Following hybridization of plaques with labeled oligonucleotides or gene fragments of FIV, positive clones can be identified. Each clone can be tested for infectivity by transfection into an established cell line. Restriction fragments of FIV-Oma subclones are cloned into a cloning vector and sequenced to determine nucleotide sequence. From the subclones, recombinant clones having desired biological properties can be constructed.

In one embodiment of the invention, a highly infectious and cytopathic recombinant clone (FIV-Oma3) was constructed from subclones that were not infectious or cytopathic. This clone serves as a basis for the other embodiments. The reconstructed clone is similar to the FIV-Oma virus in its cytopathic and infective abilities in tissue culture. The clone, FIV-Oma3, also serves as the basis for making chimeras having desired immunogenic and cytopathic properties.

In another embodiment of the invention, antigens from FIV-Oma and the reconstructed FIV-Oma3 are provided that have broad serological cross reactivity with related antigens from other species of FIV. The antigens of the present invention comprise polypeptides derived from the genes of FIV-Oma or FIV-Oma3. Polypeptides will be at least six amino acids found contiguously within one of the proteins of FIV-Oma or chimeric viruses. Polypeptides will generally correspond to at least one epitopic site which is characteristic of a FIV strain. By characteristic, it is meant that the epitopic site will allow immunological detection of the virus in a physiological sample. These antigens can be used in the detection of FIV infection of cats, both domestic and non-domestic, and for immunization of these cats.

In still another embodiment, chimeric viruses are provided having desired biological properties. Chimeras have the advantage of reduced risk of recombination within the host cells with resultant production of infectious viral particles. The recombinant immunogenic virus is preferably one that has reduced pathogenicity. For example, in one illustration of this embodiment, chimeric viruses can be constructed that are infectious in cell lines and have immunogenic properties. Such virus can be used for eliciting an antibody response in cats for the purpose of protection against FIV and could be easily propagated in established cell lines. The recombinant virus may contain gag, pol, vif, rev and other viral proteins or combinations thereof. In another illustration, a chimeric virus may be both pathogenic and infectious in cats. Such cats would then serve as a model system for evaluating antiviral compounds and a tool for investigating FIV infection.

In yet another embodiment, DNA constructs are provided which can be expressed using expression vectors well known in the art. An expression vector typically has a DNA construct linked to control sequences capable of expressing that DNA in a suitable host. Generally such control sequences include a transcriptional promoter, an optional operator sequence to control transcription, a sequence encoding suitable mRNA, and sequences which control the termination of transcription and translation. Suitable vectors include plasmids, viruses, including, but not limited to, vaccinia virus, adenovirus, baculocirus and cytomegalovirus and phages.

These and other applications of the present invention will become more clear from the following examples.

EXAMPLE 1

Propagation of FIV-Oma

For propagation and maintenance of FIV-Oma, any of the cell lines known in the art can be used, including cells in suspension and substrate-attached cells. For example, Crandell feline kidney cells (CrFK) which grow as a monolayer or interleukin (IL)-2 dependent T-cell lines which grow as cells in suspension and require I1–2, can be used (Yamamoto et al. U.S. Pat. No. 5,510,106). Other T-cell lines that do not require IL-2 can also be used.

To further illustrate this embodiment, virus cultures of FIV-Oma were inoculated onto CrFK cells at 50% confluency and cultured in the presence of complete CrFK growth medium (minimum essential growth medium with 20% Leibovitz's L-15 medium 4 mM L-glutamine, 1% gentamicin, and 5-fetal bovine serum). Numerous small syncytia were observed 3 to 4 days after inoculation of CrFK cells with FIV-Oma cultures. Following passage of the CrFK cells, numerous large syncytia (greater than 20 nuclei) and extensive cellular vacuolation were detected at confluency; and the CrFK monolayer was completely lysed 4 to 5 days after passage. The virus maintained this degree of cytopathy over subsequent passages through CrFK cells. This virus can also be propagated in peripheral blood mononuclear cells (PBMCs). For inoculation of PBMC cultures, cell-free medium from day 3-transfected CrFK cell culture was inoculated onto concanavalin A and IL-2 stimulated PBMCs. Supernatants from PBMC cultures can be assayed for reverse transcriptase activity, filtered through a 0.22 $\mu$m pore size filter and then used for further inoculation.

EXAMPLE 2

Production and Screening of the Genomic DNA Library

A genomic library was constructed in a lambda phage vector. FIV-Oma infected CrFK cells were grown to confluency in CrFK growth medium as described in Example 1. The cells were divided 1:5 once after 3 days of cultivation and were monitored daily for syncytium formation. When large syncytia were noted, genomic DNA was isolated and a genomic DNA library constructed in accordance with standard procedures well known in the art (See W. Strauss, Preparation of genomic DNA from mammalian tissue, in *Current Protocols in Molecular Biology,* pp 2.2.1–2.2.3, F. Ausubel, R. Brent, R. Kingston, D. Moore, J. Seidman, J. Smith and K. Struhl, eds. 1989; Green Publishing Associates and Wiley-Interscience, New York). Briefly, cells were lysed, digested and phenol:chloroform:isoamyl alcohol extracted according to Sambrook et al (1989). DNA was precipitated in ethanol, resuspended in Tris-EDTA buffer containing 0.1% Sodium dodecyl sulfate and 25 ug/ml RNase A, incubated for 48 hours at 37° C., and dialyzed for 24 hours against 50 mM Tris-HCl, 10 mM EDTA, pH 8.0. Following partial digestion with Sau3A, 10–20 kb fragments were selected by centrifugation on a 5 to 25% NaCl gradient. The fragments were ligated into EMBL-3 phage vector at the Bam H1 cloning site and packaged using a bacteriophage packaging extract (Gigapack II from Stratagene).

For expression and screening of the genomic library, the extract from the packaging extract was plated on E. coli (strain P2392), and plaques screened by using a $^{32}$P-labeled FIV-Oma pol gene fragment (Barr et al., 1995). The pol gene fragment was made using degenerate lentivirus pol primers described in Gelman et al (1992, *AIDS Res. Hum. Retroviruses* 8:1981–1989. These primers amplified a 437 bp fragment from DNA isolated from CrFK culture infected with the Pallas FIV. The degenerate primer sequences used for amplification were LV1: CCGATCCDCAYCCNGSAGGAYTAMAA (SEQ ID NO:14), and

LV2: GGTCTAGAYRYARTTCATAACCCAKCCA (SEQ ID NO:15)

where Y=C or T; R=A or G; S=C or G; M=A or C; D=G,T or A; and K=G or T.

Bacteriophage from positive plaques were purified and amplified according to instructions of the manufacturer of the packaging extract, and bacteriophage preparations were banded on cesium chloride gradients (Sambrook et al. 1989). Following dialysis in 0.1 M Tris-HCl, pH 8.0, 0.05 M NaCl, 1 mM $MgCl_2$, DNA was prepared from the FIV-Oma positive clones by proteinase K digestion (50 mM EDTA, pH 8.00, 50 SDS, 100 ug/ml proteinase K), phenol chloroform extraction and ethanol precipitation.

EXAMPLE 3

Subcloning and Sequencing of Lambda Clones

FIV-Oma positive clones from Example 2 were digested with restriction enzymes BamH1, EcoR1, HindIII, KpnI, NheI, PstI, SacI, and SalI. Fragments were separated by agarose gel electrophoresis, and detected by Southern hybridization using $^{32}$P-labeled FIV-Oma pol fragment. Restriction enzyme fragments of the clones were purified from agarose gels using a DNA recovery system (SpinBind system from FMS Bioproducts) and ligated into a phagemid cloning vector (pBlueScript II, SK-from Stratagene). Nucleotide sequencing was performed using standard primers to vector sequences and FIV-Oma-specific primers to obtain data for both strands of DNA. The sequencing was performed using automated DNA sequencing and conventional chain termination sequencing (Isotherm DNA sequencing kit; Epicentre Technologies). The sequence was analyzed using commercially available software.

Figure 1B:
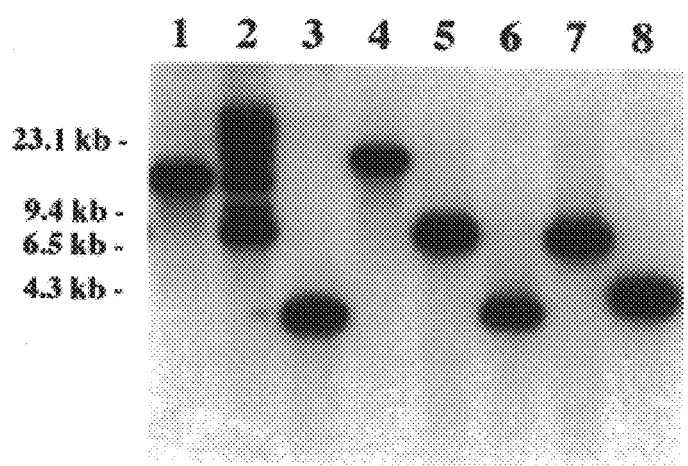
FIG. 1B is a photomicrograph of a Southern blot illustrating endonuclease Pst1 digestion of the lambda clones of FIV-Oma.

Eight positive lambda clones ($\lambda 1-\lambda 8$) were isolated from the genomic library using the FIV-Oma pol gene probe from Example 2. Using the pol probe, several 4.0 kb Sacd fragments, and a 7.0-kb Pst1 fragment were identified in lambda clones 1,2,4,5,7, and 2,5 and 7 respectively (FIGS. 1A and 1B). Southern blots were also hybridized with $^{32}$P-labeled FIV-Oma viral cDNA to detect additional viral fragments. Based on the degree of heterogeneity in restriction patterns of the clones, it was inferred that all clones except $\lambda 2$ clone were less than full length. Out of the eight clones, three (clones 2, 5, and 7) had 4.0 kb Sacd fragment as well as the 7.0 kb Pst1 fragment. FIV-Oma $\lambda 5$ and $\lambda 7$, both of which have an internal Sac1 and Pst1 fragments, were used for nucleotide sequence analysis in a cloning vector using vector-specific and FIV specific primers. Subclones of partially overlapping restriction fragments were then sequenced. Based on this analysis, it was inferred that proviral clone 7 was truncated at the 3' end while proviral clone 5 was integrated aberrantly (3' gag, pol, env, partial 3' LTR, 5'LTR, 5' gag). Clone $\lambda 2$ was the only full length proviral clone containing 5' and 3' LTRs in the correct position.

EXAMPLE 4

Characterization of Lambda Clones

Illustrated in this embodiment is the determination of infectivity of proviral clones. To determine infectivity, each clone can be transfected into a cell line by methods well known in the art, for example using calcium phosphate, DEAE-Dextran and electroporation (see R. Kingston et al., in *Current Protocols in Molecular Biology,* supra pp 9.0.1–9.4.3). To further illustrate this embodiment, each clone from Example 3 was transfected into CrFK cells using commercial calcium phosphate reagent (CellPhect Transfection kit; Pharamcia). Briefly, 5–10 µg DNA was mixed with an equal volume of Buffer A (0.5 M $CaCl_2$, 0.1 M HEPES, pH 7.), incubated at room temperature for 10 minutes, mixed with an equal volume of Buffer B (0.28 M NaCl, 0.05 M HEPES, 0.75 mM $NaH_2PO_4$, 0.75 mM $Na_2HPO_4$, pH 7.0), incubated at room temperature for another 15 minutes, and added to 50% confluent CrFK cells. The cells were incubated at 37° C. for 4–6 hours, then subjected to a glycerol shock. For the glycerol shock, the cells were washed once with HBSS and incubated with 20% glycerol in phosphate-buffered saline (PBS) for 1.5 minutes, then washed twice with HBSS. After glycerol shock, the cells were incubated in growth medium at 37° C. Supernatants from transfected cells were harvested daily and observed for virion production by assaying for reverse transcriptase activity according to the method of Heine et al., 1980, which method hereby incorporated by reference. Briefly, supernatant samples (10 µl/reaction) were incubated at 37° C. for 1 hour in a 40 µl solution containing 20 mM KCl, 50 mM Tris, pH 7.8, 20 mM $MgCl_2$ (or 0.6 mM $MnCl_2$), 2 mM dithiothreitol (DTT), 1 µg poly (rA) as template, oligo(dT)$_{12-18}$ as primer, and [$^3$H]TTP. The mixture was spotted onto an ion-exchange paper (DE81 from Whatman) and washed five times with 2% $Na_2HPO_4$, once with $dH_2O$, and once with 95% ethanol. The paper was dried, and incorporated radioactivity was counted in a Beckman Scintillation spectrometer. Based on the RT assays, virus production was not evident in any of the transfected cells at any time for up to 5 weeks after transfection, indicating that none of the eight clones were replication competent and infectious.

EXAMPLE 5

Construction of a Recombinant Clone

Since none of the proviral clones were found to be infectious, recombinations of the clones were carried out. An infectious clone was constructed from three of the proviral clones, $\lambda 2$, $\lambda 5$ and 7.

5.1 Amplification of FIV-Oma Sequences

Sequences of $\lambda 2$ were amplified by polymerase chain reaction (Saiki et al. 1988) by methods well known in the art and using commercially available reagents (GeneAmp; Perkin-Elmer Cetus). Briefly, 1 µg of DNA template, 1 µg of each primer, dNTPs (0.2 mM each), 2 mM $MgCl_2$ and 5 Units Taq DNA polymerase was subjected to a 2-min "heat-shock" step at 95° C. prior to 30 cycles of amplification at 94° C. for 1 minute, 55° C. for 2 minutes, 72° C. for 3 minutes and a final cycle of 72° C. for 10 minutes in a commercial thermocycler. The products were cloned into a cloning vector (pCRII vector, TA cloning kit; Invitrogen corp.) and the sequence was confirmed by nucleotide sequencing.

5.2 Construction of Full-Length Virus Clone FIV-Oma1

The following FIV-Oma specific primers were used to amplify the 5' end region (1–3633 bases): forward primer 5'-GCGGCCGCTGGGAGGATTGGAGGTCCT-3' (SEQ ID NO:1), corresponding to bases 1–19 with an added 5' NotI site, and reverse primer 5'-GCTCTTAAGGCTATGTCGCA-3' (SEQ ID NO:2). Then the 1–3633 region was cut out of this subclone with NotI and AflIII, and ligated into a NotI and AflII digested subclone of $\lambda 7$ clone which contained the 7 kb region of the proviral genome in phagemid cloning vector (pBluescriptII SK-from Stratagene), to construct a 8.4 kb subclone.

Similarly, the 3' end of the provirus genome was amplified by nucleic acid amplification techniques like polymerase chain reaction (PCR). Thus, the 3' end was amplified from $\lambda 2$ clone with primers 5'-TGTCCAGTGTTAGAGTCGGTAG-3' (SEQ ID NO:3) corresponding to bases 7182–7203, and a reverse primer 5'-GTCGACTGCTAAGGTCTCCGTCCCGAATC-3' (SEQ ID NO:4), corresponding to bases 9747–9725 of the FIV-Oma genome. A TAl clone was obtained by amplification of fragments from λ2 by PCR using primers having the sequence of SEQ ID NO:3 and SEQ ID NO:4. The amplified products were cloned into PCRTMII (Invitrogen), and then removed by restriction enzyme digestion. Then the 7182–9747 base region was cut out of TA1 with Eco47III and SalI, ligated to the EcoIII and SalI digested 8.4 kb subclone to construct a full length FIV-Oma1 in a proviral vector.

5.3 Construction of Infectious Clone FIV-Oma3

Subclone TA5 was constructed by amplification of fragments from λ2 by PCR using primers having the sequence of SEQ ID NO:1 and SEQ ID NO:2. The amplified products were cloned into pCRTMII (Invitrogen), and then removed by restriction enzyme digestion. Subclones TA1 and TA5 were subjected to digestion with restriction enzymes, Eco47III and NotI. The region between Eco47III and NotI sites of the virus genome in subclone TA1 was replaced by that region in subclone TA5 to obtain a subclone TA3 containing 3' end region of the virus genome with 7297 bases derived from λ5 clone. The 3' end region (7182–9747 bases) digested from TA3 with Eco47III and SalI was cloned into similarly digested 8.4 kb subclone to construct an infectious clone FIV-Oma3.

EXAMPLE 6

Characterization of the Subclones

This embodiment is directed towards determining the infectivity and cytopathicity of the subclones constructed from the lambda clones in Example 5.

6.1 Characterization of Subclone FIV-Oma1

Following transfection of this clone into CrFK cells by calcium phosphate method as described in Example 4, a short period of particle-associated reverse transcriptase activity was noted; however, the virions did not infect either CrFK cells or feline PBMCs. Cotransfection of pFIV-Oma1 with a subclone containing the env gene from 5 resulted again in a short period of RT activity on day 3 followed by a second period on Day 13 and exponentially increasing RT activity by Day 15, suggesting that the progeny virions were able to infect and spread in the transfected cell culture. Supernatants from the FIV-Oma1/λ5 env transfection contained virus which was infectious for new cultures of CrFK cells and feline PBMCs. Because this cotransfection was successful, it was concluded that the env gene (of the overlapping first exon of rev) or FIV-Oma1 was the defective portion (persistence of infection was probably due to env recombination events). Through a series of subcloning steps outlined in Example 5, an Eco47III/NdeI fragment of FIV-Oma1 containing the env orf was replaced with the same fragment from λ5. Thus, the proviral clone, designated as FIV-Oma3 was produced.

6.2 Characterization of FIV-Oma3

Figure 2:
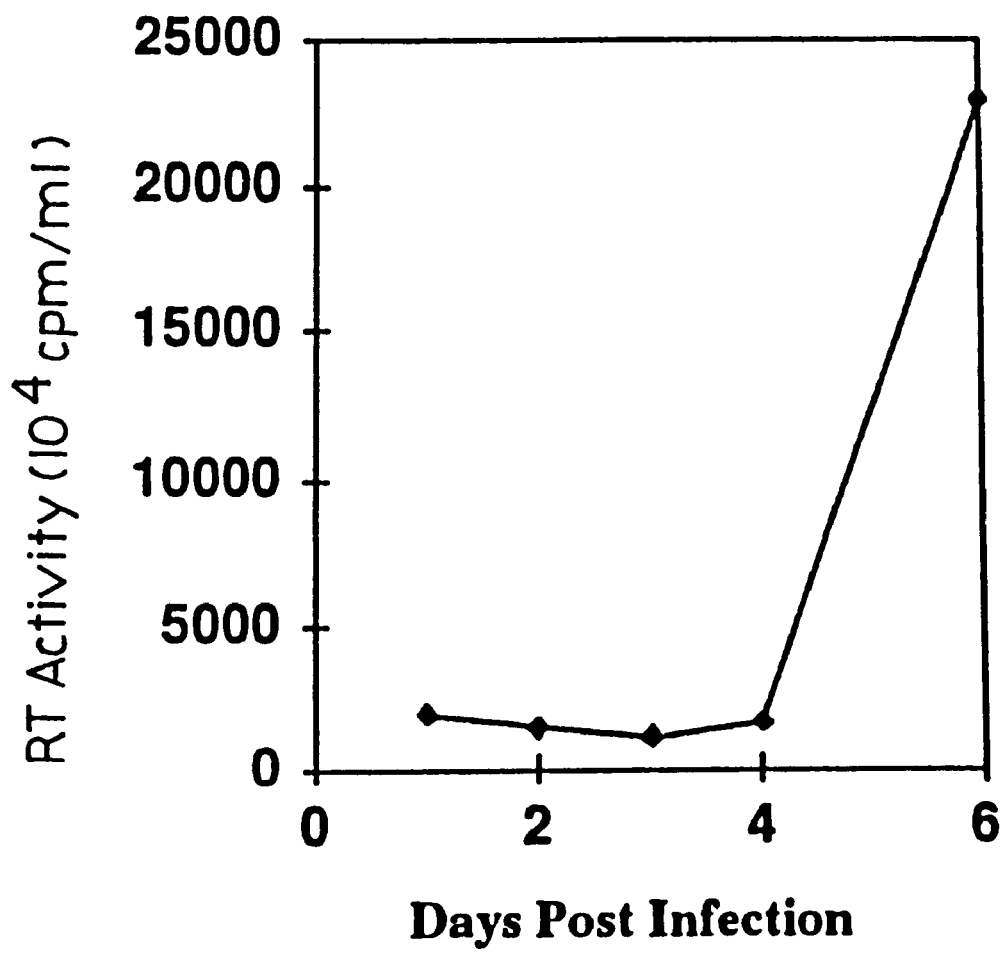
FIG. 2 is a plot of reverse transcriptase activity in CrFK cells as a function of time after infection with FIV-Oma3.

CrFK cells were transfected with pFIV-Oma3 by the calcium phosphate method as described in Example 4 to determine if the proviral clone was infectious. Infectivity of virions derived from the CrFK cells transfected with pFIV-Oma3 was determined. One ml cell-free medium from transfected CrFK cells was inoculated onto about 60% confluent CrFK cells. The RT activity in the medium was about $1.37 \times 10^8$ cpm/ml. As shown in FIG. 2, infectious virions were produced in CrFK cells. Cytopathic effect of syncytium formation and vacuolization similar to those described for wild-type FIV-Oma (Barr et al. 1955) were visible by Day 5, and most cells were lysed by Day 11 following transfection. Additionally progeny virions were infectious and cytopathic for CrFK cells and primary feline PBMCs.

EXAMPLE 7

Sequencing of FIV-Oma3

Figure 3:
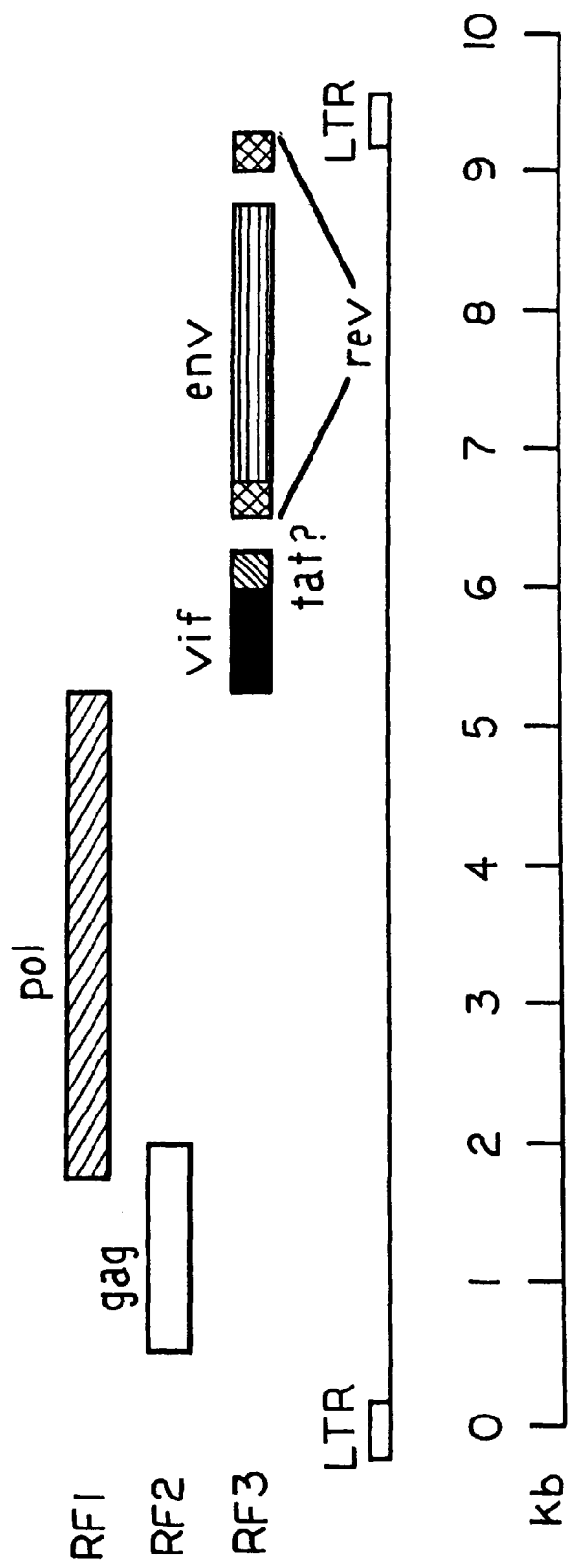
FIG. 3 is a schematic illustration of the genomic organization of FIV-Oma3.

The DNA sequence of the reconstructed clone can be determined by any of the standard methods known in the art. Using the dideoxynucleotide chain termination method in an automated DNA sequencer, the FIV-Oma3 clone was sequenced. The length of the infectious clone was found to be 9751 bp (SEQ ID NO:7). Potential regulatory and coding regions in the FIV-Oma3 provirus were identified by sequence analysis. As illustrated in FIG. 3, the genomic organization of the FIV-Oma3 provirus is typical of other lentiviruses (Narayan and Elements, 1989, *J. Gen Virol.* 70:1617:1639) with LTRs, gag, pol, env and putative vif, tat, and rev open reading frames Several additional small ORFs are also present. The open reading frame for gag protein starts at nucleotide 684 and encodes a protein of 498 amino acids (SEQ ID NO:8). The open reading frame for the pol protein begins at nucleotide 1979 and encodes a protein of 1150 amino acids (SEA ID NO:9). The open reading frame for vif protein starts at nucleotide 5429 and encodes a protein of 252 amino acids (SEQ ID NO:10). The open reading frame for the env and rev proteins starts at nucleotide 6512 and encodes a rev protein of 863 amino acids (SEQ ID NO:11). Splicing of this protein at amino acid 103 results in the formation of the env protein. Four other open reading frames, orfA (SEQ ID NO:12), orfB (SEQ ID NO:13), orfC (SEQ ID NO:14) and orfE (SEQ ID NO:15) are also present starting at nucleotides 1100, 6387, 7827 and 9165 respectively, and encoding putative polypeptides of 51, 39, 38 and 65 amino acids respectively.

To determine the extent of homology between this clone and known FIVs, the sequence of this clone was compared with three domestic cat isolates and a puma isolate. As shown in Table 2, a comparison of the nucleotide sequences for gag, pol, env, and vif proteins indicates a homology between 50–72% while that for the deduced amino acid sequence is between 36–71%. The greatest homology is seen for the pol gene.

TABLE 1

| | % similarity with FIV-Oma | | | |
|---|---|---|---|---|
| | gag (NA/AA) | pol (NA/AA) | env (NA/AA) | vif (NA/AA) |
| FIV-Fca(TM2) | 55/63 | 72/71 | 44/26 | 60/54 |
| FIV-Fca(FIV-14) | 60/63 | 72/71 | 44/26 | 52/52 |
| FIV-Fca(PPR) | 62/63 | 72/71 | 43/25 | 52/52 |
| FIV-Fco(PLV-14) | 55/52 | 63/59 | 58/47 | 50/63 |

FIV-Fca denotes domestic cat FIV strains, TM2 and FIV-14 are sequenced viral isolates, FIV-PPR is an infectious clone of a domestic cat isolate. FIV-Fco is a sequenced puma (nondomestic cat) FIV isolate (Langley et al., 1994, *Virology* 202:853–864).

EXAMPLE 8

Identification of Polypeptides which Affect Immunogenicity

This embodiment is directed towards construction of chimeric viruses to determine which sequences are required for eliciting an immune response in cats. DNA isolated from FIV-Oma3 and a selected FIV can be treated with various restriction enzyme combinations, and specific portions ligated together in constructing the chimeras. It will be appreciated by those skilled in the art that a restriction enzyme or combination of restriction enzymes may be used to generate chimeric viruses that have the desired biological properties. For example, a chimeric virus can be constructed which elicits an immune response in cats. Restriction enzyme selection may be done to reduce the cytopathicity of the immunogenic peptide. Alternatively, a chimeric virus for use as a vaccine, can be constructed which is immunogenic, and is highly infectious in cell cultures so that it may be propagated easily to obtain high titres. Further, chimeric viruses can be constructed that are highly infectious and pathogenic in cats. Such chimeras can serve as models for evaluating potential anti-viral compounds and would provide a model system for studying FIV infection.

In accordance with the methods described in Example 1., chimeric viral clones can be introduced into CrFK cells and tested for immunogenicity by techniques well known in the art including immunoblotting and western blotting.

EXAMPLE 9
Identification of Polypeptides Which Affect Cytopathicity

This embodiment is directed towards methods for identification of sequences affecting cytopathicity. Chimeras from Example 8 can be individually introduced into CrFK cells. Transfected cells are passaged every three days and carried for 3–8 passages. Cells are monitored for syncytium formation and vacuolization from Day 4. Cytopathic activity can be correlated with the specific nucleotide sequence of the clones and thus polypeptides that affect or cause cytopathicity can be identified.

EXAMPLE 10
Expression of FIV-Oma3 Polypeptides

This embodiment illustrates that the DNA fragments from FIV-Oma3 or chimeric viruses constructed therefrom as in Example 8, may be incorporated in DNA constructs capable of introduction into expression vectors such as phage vectors or plasmids. The DNA construct should contain the necessary elements for transcription and translation. A variety of host systems may be utilized to express the Oma or chimeric peptides including, but not limited to, bacteria transformed with a bacteriophage vector, plasmid vector, or cosmid DNA; yeast containing yeast vectors, fungi containing fungal vectors, insect cell lines infected with virus (e.g. baculovirus); avian cells transfected with plasmid or viral expression vectors, or infected with recombinant virus; and mammalian cell lines transfected with plasmid or viral expression vectors, or infected with recombinant virus (e.g. vaccinia virus, adenovirus, adeno-associated virus, retrovirus, etc.) To increase the expression of the polypeptides, various promoters and enhancers can be incorporated in the DNA vector by methods well known in the art. A broad variety of suitable promoters are available. The selection of the promoter depends on the expression system used. Promoters vary in their ability to facilitate transcription. Generally, for the purpose of expressing a cloned gene, it is desirable to use a strong promoter in order to obtain a high level of transcription of the gene and expression into gene product. Suitable promoter systems in microbial expression vectors include the beta lactamase and lactose promoter systems, tryptophan promoter system and the tac promoter. Suitable promoters for yeast vectors include the promoters for metallothionein, 3-phosphoglycerate kinase or other glycolytic enzymes. For insect cells as host cells, the polyhedrin or p10 promoters of baculovirus can be used. For mammalian cells, promoters such as SV40 early or late promoters and the metallothionine-I promoter can be used.

Other regulatory elements for efficient gene transcription or message translation include enhancers, and regulatory signals. Enhancer sequences are DNA elements that appear to increase transcriptional efficiency in a manner relatively independent of their position and orientation with respect to a nearby gene. Thus, depending on the host cell expression vector system used, an enhancer may be placed upstream or downstream from the inserted nucleotide sequence. One or more regulatory elements, such as transcription or translation initiation signals may be used to regulate the expression of the nucleotide sequence encoding the recombinant polypeptide.

The polypeptides of the present invention may be modified using genetic engineering techniques. For, example, site directed mutagenesis may be used to change a single amino acid in the polypeptide to alter its immunogenic and/or its cytopathic activity.

Figure 4:
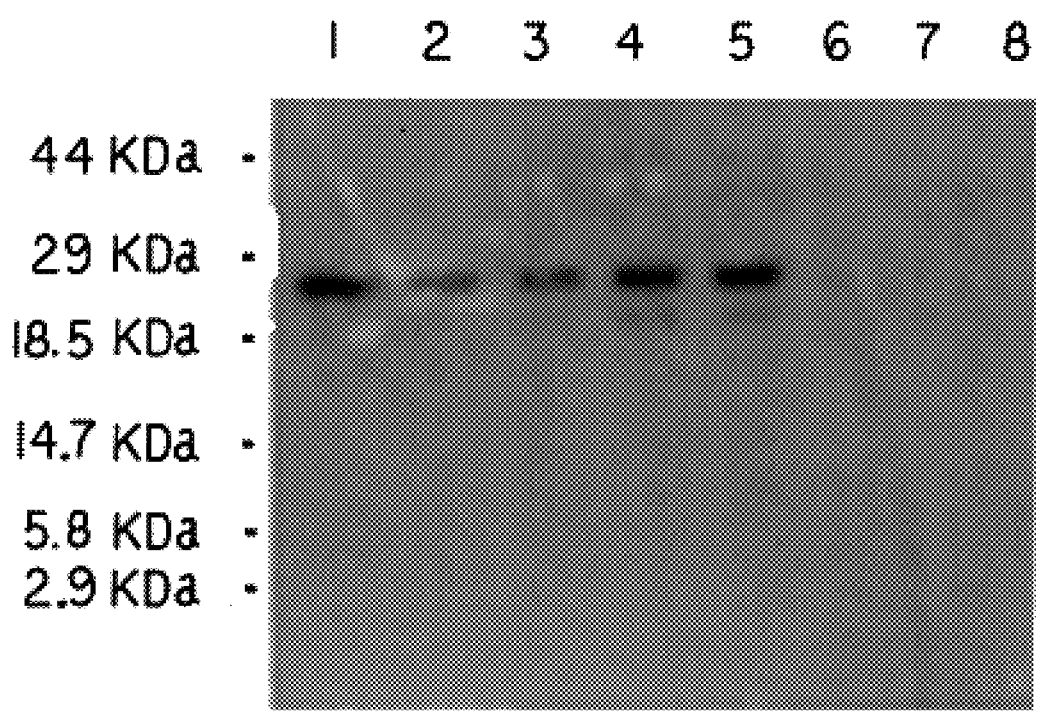
FIG. 4 is a representation of a western blot illustrating the presence of purified vif protein in eluted fractions.

To further illustrate this embodiment, the vif gene was PCR amplified from lambda 2 clone using primers 5'-GCTACCGAGTGGTGAAGAGGATTGGCAG-3' (SEQ ID NO:5) and 5'-GTCGACTTAACTCTTCATCCG-3' (SEQ ID NO:6). DNA was ligated to PCRTMII vector (Invitrogen) to obtain a subclone containing the vif gene (without a start codon). Then the vif gene was cut out of this subclone with KPNI and SalI and ligated to KpnI and SalI digested $pQE_{31}$ vector (Qiagen) to construct a vif expression clone vif/$pQE_{31}$. Selected *E.coli* transformants of vif/$pQE_{31}$ were grown in the presence of ampicillin and kanamycin. After they reached an appropriate cell density ($OD_{600}$=0.7–0.9), 2mM IPTG was added to induce protein expression. The cells were grown for several additional hours to allow protein expression before they were harvested. Then the cells were lysed in Buffer A (6 M GuHCl, 0.1 M Na-phosphate, 0.01 M Tris/HCl, pH 8.0) at 5 ml per gram wet weight for 1 hour at room temperature. After a series of washing steps with Buffer A, Buffer B (8 M urea, 0.1 M Na-phosphate, 0.01 M Tris/HCl, pH 8.0) and Buffer C (8 M urea, 0.1 M Na-phosphate, 0.01 M Tris/HCl, pH 6.3) until the $A_{280}$ of the flow-through was less than 0.01, the recombinant protein was eluted with Buffer C containing 250 mM imidazole. The eluted fractions were collected and analyzed on 15% SDS-PAGE by methods well known in the art. As shown in FIG. 4, SDS-PAGE analysis of purified His-tagged vif protein indicates the presence of approximately 22 kD protein in fractions 1–5.

In another illustration of this embodiment, the gag gene was amplified by PCR using primers Bam-gag and gag-Xho from 1 ng of pOma3. The BamHI-XhoI digested product was cloned into pET28(a)(Novagen) that had been digested with BamHI and XhoI. The recombinant pET-Gag plasmid was transformed into BL21(λDE) cells. Induction of the gag polyprotein was accomplished by the addition of IPTG to the culture at 1 mM, with growth for an additional 4 hours at 37° C. Bacterial extract was prepared in and run on 8–20% Phast gels (Pharmacia) according to manufacturer's instructions.

EXAMPLE 11
Vaccines and Vaccine Formulations

This embodiment is directed towards various vaccines useful for protecting cats against FIV. Examples of vaccines useful for protecting cats against FIV include live attenuated chimeric viruses, fixed whole viruses, host cells which express viral antigens, preparations of viral fragments, purified proteins from the viruses or expressed by host cells, and antigenic fragments of proteins.

Live attenuated virus is made by serial passage of the virus in CrFK cells in culture, or genetically altering it in accordance with procedures well known in the art. For preparing fixed virus, live virus is contacted with a suitable fixative like formalin. Fixed virus can then be used in vaccine formulations.

Alternatively, the polypeptides of FIV-Oma1 or FIV-Oma3 may be expressed in a suitable host system as described in Example 10. Recombinant polypeptides produced can be purified by methods well known in the art including detergent extraction, chromatography (e.g. ion exchange, affinity, immunoaffinity, or sizing columns), differential solubility, differential centrifugation, and the like. Immunopurification of the polypeptides from a host cell expression system preparation may be accomplished using methods known in the art for immunoaffinity chromatography. Specific antibodies for desired epitopes may be linked to a solid matrix to form an affinity matrix. The preparation containing the recombinant polypeptides is then incubated with the affinity matrix. The affinity matrix is washed to remove unbound material and the bound peptide is then eluted from the matrix.

Transformed host cell preparations can also be used in vaccines. The lysate from the host cell preparation may be used in a crude form or the expressed polypeptides can be purified by conventional methods. Alternatively, host cells such as yeast cells may be transformed with vectors so that polypeptides of the present invention are expressed on the surface of the yeast cells. The yeast cells can then be used in a vaccine either as such or fixed in a suitable fixative.

Vaccine formulations of the present invention comprise the antigen in a pharmaceutically acceptable carrier. The antigen is present in an amount sufficient to elicit an immune response. Optionally, one or more adjuvants may also be present. The adjuvants aid in attaining a more durable and higher level immune response using smaller amounts of vaccine antigen or fewer doses than if the vaccine antigen were administered alone. Suitable adjuvants include Freund's adjuvant, Adjuvant 65 (containing peanut oil, mannide monooleate and aluminum monostearate), mineral gels such as aluminum hydroxide and aluminum phosphate, plant and animal oils and synthetic polymers. The vaccine formulation may also contain a stabilizer like a carbohydrate (sorbitol, mannitol, glucose, starch) or a protein (albumin or casein).

The vaccines of the present invention may be administered by any conventional means. Examples of suitable administration routes are intramuscular, subcutaneous, oral, nasal, and intraperitoneally. The dosage of the immunogen depends upon the immunogen and the route of administration. Typically, a single dose has a total volume of between about 0.1 ml to 5.0 ml.

The number of inoculations should be sufficient to elicit an immune response. Determination of the number and temporal spacing of the inoculations is well within the skill of those skilled in the art. In general, there are at least two inoculations spaced over a period of two to ten weeks.

Figure 5:
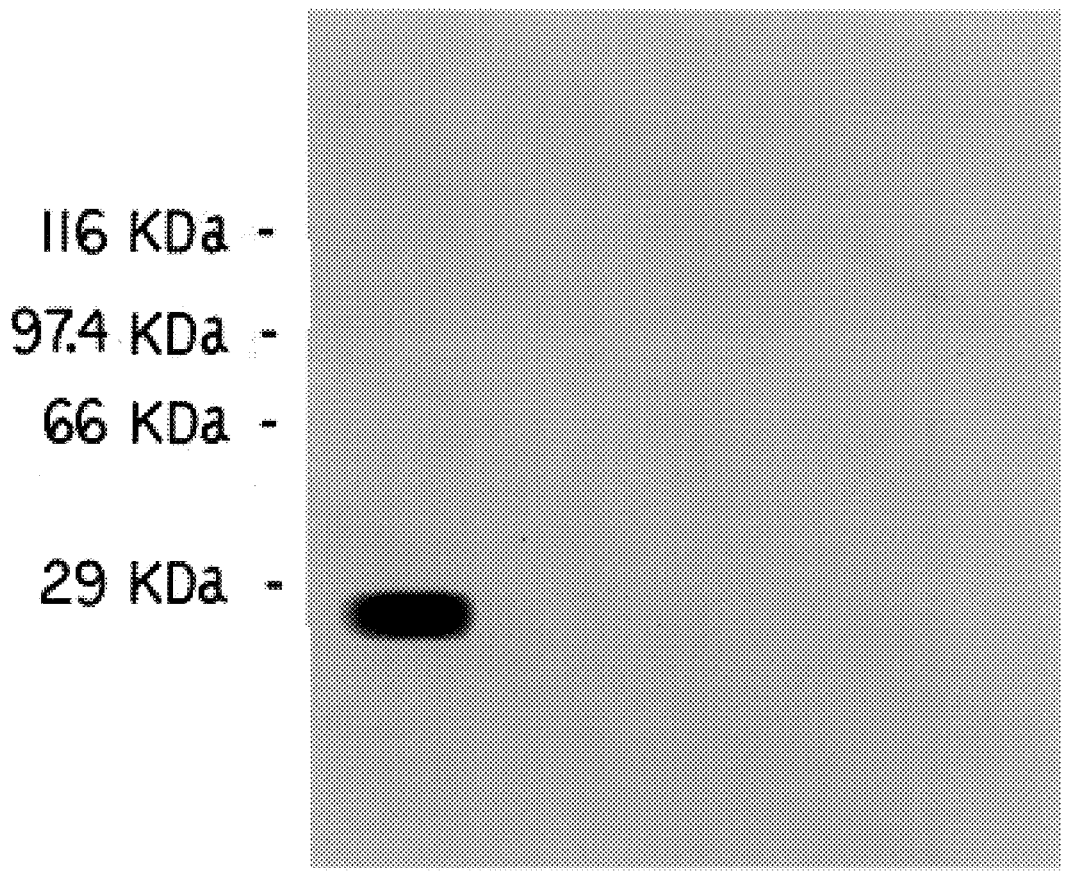
FIG. 5 is a representation of a western blot of vif protein indicating the presence of specific antibodies in rabbit sera immunized with vif protein.
Figure 7A:
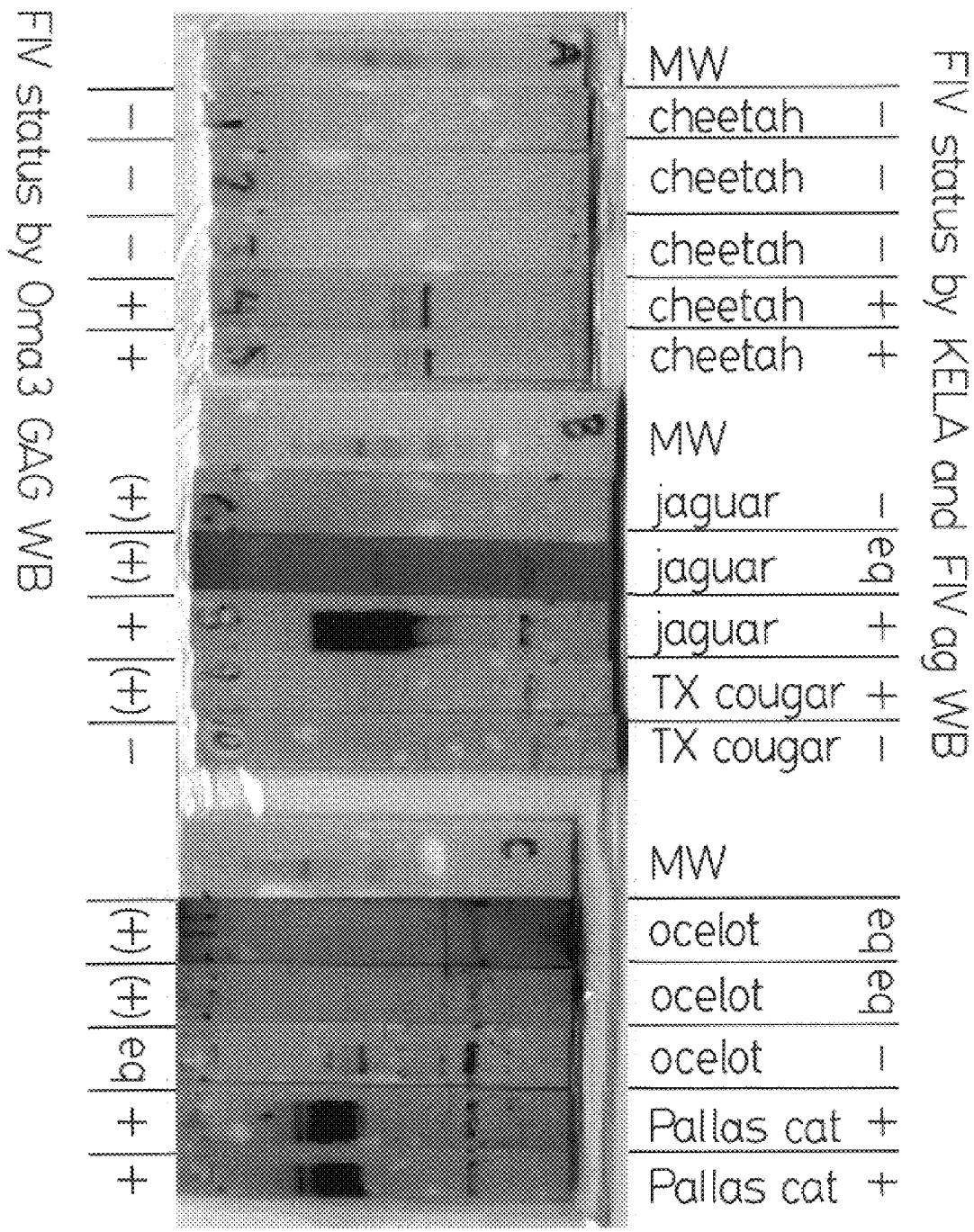
Figure 7C:
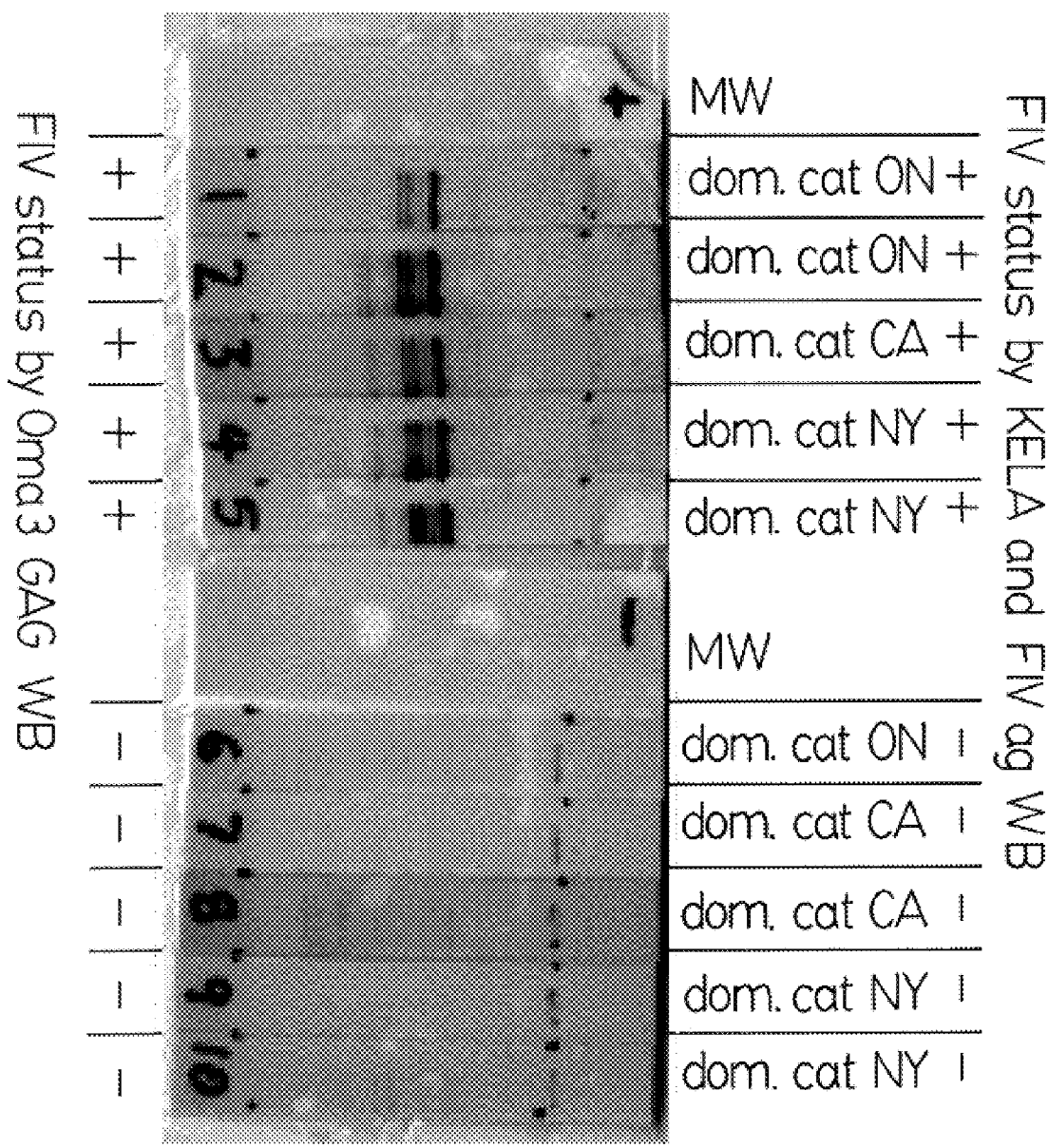

In one illustration of this embodiment, purified vif protein from Example 10 was used to produce polyclonal antibodies in rabbit by standard methods known in the art and as described in this embodiment. Antiserum from the immunized rabbit was collected. Western blotting was performed to detect the presence of vif antibodies in the rabbit serum. As shown in FIG. 5, the rabbit antiserum contained antibodies that reacted specifically with purified vif protein. This demonstrated the efficacy of FIV-Oma3 polypeptides for the generation of antibodies.

Similarly, since the gag gene and its predicted protein have been reported to be highly conserved among the isolates of FIV, the gag protein from FIV-Oma or from a chimeric virus from Example 9, can be used in the vaccination of cats.

EXAMPLE 12

Detection Systems for FIV

This embodiment is directed towards reagents and methods for detecting the presence of FIV antibodies in cats. Preferably, the reagents can be used for detection of FIV strains of both domestic and non-domestic cats. Detection system of the present invention may involve detection by polynucleotide probes or by polypeptides.

12.1 Polynucleotide Probes

Detection of FIV in biological samples can be carried out using polynucleotide probes based on the sequence of the FIV genome. The length of the probe is not critical but is preferably at least 12 bases and is sufficiently complimentary to the viral genome. The probe may be DNA or RNA. DNA probes may be prepared synthetically or may be prepared by cleavage of the genome by restriction endonucleases followed by cloning of the DNA fragment to obtain large quantities by techniques well known in the art. The probes can be labeled according to standard techniques. The labels may be radioactive (e.g. $^{14}C$, $^{32}P$ or $^{3}H$) or non radioactive such as specific antibodies, fluorescers, chemiluminescers, and enzymes. Commonly used labeling techniques for radioactive labeling include nick translation with alpha $^{32}P$ labeled d[NTP] or end labeling using T4 polynucleotide kinase and gamma $^{32}P$-NTP. Labeled probes can be purified on polyacrylamide gels with subsequent elution in distilled water. (Sambrook et al 1989).

The probes are then used to detect the presence of FIV by hybridization techniques that are well known in the art. As those skilled in the art will recognize, stringency conditions during hybridization can be varied to identify either closely related strains or a wide variety of strains. The more stringent the incubation condition, the higher the degree of complimentarily that is required between the probe and the sample DNA. Stringency can be controlled by temperature, probe concentration, probe length, ionic strength, time etc. A common way of varying stringency is to vary the concentration of formamide to change the polarity of the reactant solution.

The diagnostic probes of the present invention include nucleotide sequences that hybridize to FIV-Oma3 genomic DNA or fragments thereof. Thus, the probes may be fragments of cDNA or oligonucleotide probes which hybridize to DNA sequences encoding FIV-Oma3 polypeptides. By selecting conserved regions of the polypeptides and synthesizing oligonucleotide probes based on the regions (or obtaining the cDNA fragment), and using stringent conditions of hybridization, FIV isolates that are closely related to FIV-Oma can be identified. On the other hand, using non-stringent condition, and/or non-conserved regions of the polypeptides, assays can be designed that will detect both domestic and non-domestic cat FIVs.

In one illustration of this embodiment, conserved regions of the FIV gene sequences can be identified using commercially available software. Oligonucleotide probes can be designed taking into consideration the degeneracy of the genetic code, which is well known in the art. By varying the stringency of hybridization condition, various strains of FIV can be detected. As an illustration of this embodiment, FIG. 6A shows homologous regions of gag protein from different strains of FIVs. The regions are particularly suitable for designing oligonucleotide and polypeptide probes. In FIG. 6B, aligned amino acid residues are printed in lowercase. Other residues (uppercase) are not aligned. Boxed areas indicate conserved regions of highest similarity. An example of a nucleotide probe based on the first conserved region is shown in FIG. 2B. 12.2 Polyeptide probes The detection system of the present invention also includes polypeptide probes which can be used as antigens in immunoassays for the detection of FIV antibodies. Antigenic peptides can be generated from the recombinant polypeptides or can be synthesized by techniques well known in the art. The antigenic peptides can vary in size but generally consist of from 7 to 14 amino acids and can be synthesized by methods including solid peptide synthesis using tertbutyl oxycarbonyl amino acids (Mitchell et al., 1978, *J. Org/Chem.* 43:2845–285); using 9-fluorenylmethyloxycarbonyl amino acids on a polyamide support (Dryland et al., 1986, J. Chem. So. Perkin Trans. I, 125–137); by pepscan synthesis (Geysan et al., 1987, J. Immunol. Methods 3:259; Proc. Natl. Acad. Sci. USA 81, 3998); or by standard liquid phase peptide synthesis. Modification of the peptides, such as by deletion and substitution of amino acids (and including extensions and additions to amino acids) and in other ways so as not to substantially detract from the immunological properties of the peptide can be carried out. For the detection of FIV, the polypeptides and the antibodies can be labeled so as to provide a detectable signal. Suitable labels include radionucleotides, enzymes, substrates, cofactors, inhibitors, fluorescent and chemifluorescent materials, magnetic particles and the like. (see U.S. Pat. No. 5,510,106) The detection of FIV may be carried out in various biological specimens including, but not limited to, blood, plasma, serum, and urine. A diagnostic assay utilizing as an antigen, peptides or polypeptides of the present invention, includes any of immunoassays known in the art including, but not limited to, radioimmunoassay, ELISAs, "sandwich" assay, immmunoblotting, fluorescent assay and chemiluminescence-based assays. Thus, for example, gag protein from FIV-Oma3 prepared according to Example 8, can be used as an antigen in an ELISA test in which the gag protein is immobilized to a selected surface, followed by blocking of unbound areas of the surface, contacting the sample containing FIV with the selected surface having the attached antigen, washing the surface to remove unbound materials, and detection of the immune complexes by standard detection means like enzyme substrate complexes or fluorescent detection systems. Consequently, a diagnostic kit for detecting FIV in domestic and nondomestic cats may comprise a peptide from FIV-Oma3 or a chimeric virus expressing a feline FIV protein that has a broad specificity, a means for facilitating contact between the sample containing FIV and the antigen (e.g. a microtitre plate) and a means for detecting presence of immune complexes formed.

To be useful in the detection methods of the present invention, the polypeptides are obtained in a substantially pure form and free of contaminants and interfering proteins. Using conventional protein purification techniques known in the art, and as described in Examples 9 and 10, polypeptides of the present invention can be purified to at least 50% purity. Suitable means of purification of proteins include affinity columns, immunoadsorption and the like. Once the peptide is purified in sufficient amount, it can be used in the detection systems of the present invention.

In one illustration of this embodiment gag protein was used in western blotting analysis to detect the presence of different strains of FIV. Gag protein prepared according to Example 10 and run on 8–20% Phast gels (Pharmacia) was transferred to nitrocellulose by capillary blot. Nitrocellulose strips were incubated with cat serum which had been pre-incubated with approximately 0.5 mg/ml *E.coli* extract (Promega) at room temperature. Various Cat serum samples were diluted 1:12. Primary antibody binding was carried out overnight at room temperature. Horseradish peroxidase labeled secondary antibody (goat anti-cat IgG) binding was carried out at room temperature for 1 hour before the peroxidase color reaction. FIGS. 7A, 7B and 7C shows a comparison of conventional tests using a combination of kinetic ELISA (KELA based on an ELISA kit, IDEXX) and western blots using FIV viral antigen prepared from a domestic cat FIV strain (Petaluma) or the FIV-Oma virus. The samples were classified as plus (+), minus (–), or equivocal (eq) based on the conventional tests. The results of the conventional tests is shown on top of each panel. The gels indicate the presence or absence of gag antibodies by western blot analysis using the gag protein and methods of the present invention. The presence (+), absence (–), or weak presence ((+)) of the antibodies is shown at the bottom. MW indicates molecular weight makers; TX cougar is Texas cougar; Af. lion is African lion; Bk.footed cat is Black footed cat; and ON is Ontario; These data clearly indicate that gag protein from the FIV-Oma3 clone detects a wide range of FIV strains and therefore, can be used to detect the presence of FIV in both domestic and nondomestic cats.

EXAMPLE 13

In another embodiment of this invention, a system is provided for evaluating the inhibitory effects of potential therapeutics of FIV. Since the infectious clone FIV-Oma3 has been found to be highly cytopathic and infectious in culture, a culture of CrFK cells can be inoculated with FIV-Oma3. The cultures can be set up in any type of tissue culture plates, preferably in a multiwell plate. Once the cells have been infected with the virus, potential inhibitory agents can be added under sterile conditions and the cultures monitored for syncytium formation and vacuolization.

From the preferred embodiments described herein, it will be apparent to one skilled in the art that various modifications may be made to the disclosed embodiments without departing from the scope of the present invention.

What is claimed is:

1. A feline immunodeficiency virus which exhibits morphological and immunological properties of the retrovirus which is designated as FIV-Oma3 (SEQ ID NO:7).

2. An isolated and purified nucleic acid molecule encoding an feline immunodeficiency virus of claim 1.

3. An isolated and purified nucleic acid molecule which encodes a polypeptide selected from the group consisting of SEQ ID NO:8, SEQ ID NO:9, SEQ ID NO:10, SEQ ID NO:11, SEQ ID NO:12, SEQ ID NO:13, SEQ ID NO:14 and SEQ ID NO:15.

4. The nucleic acid molecule of claim 3, wherein the polypeptide is SEQ ID NO:8.

5. The nucleic acid molecule of claim 3, wherein the polypeptide is SEQ ID NO:9.

6. The nucleic acid molecule of claim 3, wherein the polypeptide is SEQ ID NO:10.

7. The nucleic acid molecule of claim 3, wherein the polypeptide is SEQ ID NO:11.

8. The nucleic acid molecule of claim 3, wherein the polypeptide is SEQ ID NO:12.

9. The nucleic acid molecule of claim 3, wherein the polypeptide is SEQ ID NO:13.

10. The nucleic acid molecule of claim 3, wherein the polypeptide is SEQ ID NO:14.

11. The nucleic acid molecule of claim 3, wherein the polypeptide is SEQ ID NO:15.

* * * * *